(12) United States Patent
Scott et al.

(10) Patent No.: US 10,258,804 B2
(45) Date of Patent: Apr. 16, 2019

(54) THERMAL MANAGEMENT FOR RECHARGE OF IMPLANTABLE MEDICAL DEVICES

(71) Applicant: Medtronic, Inc., Minneapolis, MN (US)

(72) Inventors: Erik R. Scott, Maple Grove, MN (US); Kunal Paralikar, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 130 days.

(21) Appl. No.: 15/343,949

(22) Filed: Nov. 4, 2016

(65) Prior Publication Data

US 2018/0126177 A1     May 10, 2018

(51) Int. Cl.
*A61N 1/37* (2006.01)
*A61N 1/378* (2006.01)
(Continued)

(52) U.S. Cl.
CPC .............. *A61N 1/3787* (2013.01); *A61B 5/01* (2013.01); *A61B 5/4836* (2013.01); *A61B 5/6867* (2013.01); *A61F 7/0085* (2013.01); *A61M 5/172* (2013.01); *A61M 5/44* (2013.01); *A61B 2560/0219* (2013.01); *A61F 2007/0052* (2013.01); *A61F 2007/0096* (2013.01); *A61M 5/14276* (2013.01); *A61M 2205/3368* (2013.01); *A61M 2205/3523* (2013.01);
(Continued)

(58) Field of Classification Search
CPC .................... A61N 1/3787; A61N 1/08; A61B 2560/0219; A61F 2007/0052
See application file for complete search history.

(56) References Cited

U.S. PATENT DOCUMENTS

| 5,434,493 A | 7/1995 | Woody et al. |
| 5,733,313 A | 3/1998 | Barreras, Sr. et al. |

(Continued)

FOREIGN PATENT DOCUMENTS

| WO | 2006121835 A1 | 11/2006 |
| WO | 2009055579 A1 | 4/2009 |

OTHER PUBLICATIONS

International Search Report and Written Opinion from International Application No. PCT/US2017/054691, dated Jan. 2, 2018, 12 pp.
"Hot & Cold Pain Relief/ Instant Relief for Chronic Headaches," SootheAway, retrieved on Oct. 28, 2015, from http://sootheaway.com/product-information/how-it-works-hot-cold-pain-relief/, 2 pp.
(Continued)

*Primary Examiner* — Tammie K Marlen
(74) *Attorney, Agent, or Firm* — Shumaker & Sieffert, P.A.

(57) ABSTRACT

Devices, systems, and techniques are configured for cooling tissue during recharge of an implantable medical device (IMD) battery. In one example, a method includes charging, by an inductive charger, a rechargeable battery of an implantable medical device (IMD) within a patient, wherein the IMD comprises a housing that houses the rechargeable battery, and wherein a primary coil of the inductive charger is positioned above a region of skin of the patient proximate to the IMD. The example method further includes cooling, by a heat exchanger, the region of skin below a normal ambient surface temperature of the region of skin, wherein the heat exchanger is interposed between the primary coil and the region of skin.

32 Claims, 11 Drawing Sheets

(51) Int. Cl.

| | | |
|---|---|---|
| *A61F 7/00* | (2006.01) | |
| *A61B 5/00* | (2006.01) | |
| *A61B 5/01* | (2006.01) | |
| *A61M 5/172* | (2006.01) | |
| *A61M 5/44* | (2006.01) | |
| *A61N 5/06* | (2006.01) | |
| *A61M 5/142* | (2006.01) | |

(52) U.S. Cl.
CPC ............... *A61M 2205/502* (2013.01); *A61M 2205/8206* (2013.01); *A61N 5/0601* (2013.01)

(56) References Cited

U.S. PATENT DOCUMENTS

| | | |
|---|---|---|
| 5,991,665 A | 11/1999 | Wang et al. |
| 7,505,816 B2 | 3/2009 | Schmeling et al. |
| 8,901,878 B2 | 12/2014 | Prutchi et al. |
| 8,974,366 B1 | 3/2015 | Radziemski et al. |
| 9,537,344 B2 * | 1/2017 | Thompson .............. H02J 7/025 |
| 2006/0247738 A1 | 11/2006 | Schmeling et al. |
| 2007/0096686 A1 | 5/2007 | Jimenez et al. |
| 2008/0272742 A1 | 11/2008 | Hart et al. |
| 2009/0082835 A1 | 3/2009 | Jaax et al. |
| 2013/0197608 A1 * | 8/2013 | Eiger .................. A61N 1/3787 |
| | | 607/61 |
| 2013/0278226 A1 | 10/2013 | Cong et al. |
| 2014/0266022 A1 | 9/2014 | Degen et al. |

\* cited by examiner

THERMAL MANAGEMENT FOR RECHARGE OF IMPLANTABLE MEDICAL DEVICES

TECHNICAL FIELD

This disclosure generally relates to implantable medical devices and, more particularly, to thermal management for rechargeable implantable medical devices.

BACKGROUND

A variety of implantable medical devices (IMDs) are used for providing medical services (e.g., monitoring and/or delivering therapy) to patients suffering from a variety of conditions. For example, IMDs may monitor one or more physiological parameters of patients to aid in diagnosis or treatment by a clinician. Further, IMDs may deliver electrical stimulation therapy to patients to treat their conditions, for example, urinary or fecal incontinence, sexual dysfunction, or gastroparesis. For example, such IMDs may be used to stimulate a target nerve or muscle to remedy chronic incontinence associated with bladder muscle weakness. These devices are intended to provide a patient with a therapeutic output to alleviate or assist with a variety of conditions. IMDs may also be used to periodically deliver drugs to a patient.

Typically, such devices are implanted in a patient and are powered by rechargeable batteries. The battery of an IMD may be recharged inductively through the skin by an inductive charger. Despite the fact that technology exists to inductively charge a battery outside of a patient within minutes, current IMD recharging techniques require multiple hours to completely recharge the battery of an IMD within a patient. If energy is transferred to the battery too rapidly, inductive charging may generate enough heat to damage the patient's tissue. Thus, other IMDs require that the inductive charger transfer energy to the battery at a slow rate to prevent heating the tissue of the patient to an undesirable temperature. Some IMDs may achieve slightly faster recharge times by throttling the rate of charging to prevent the temperature of the IMD from exceeding a level harmful to the patient. However, these techniques remain cumbersome and time-intensive. Even with dynamic throttling of recharge rates, the patient still is required to remain in place and keep the inductive recharger properly positioned for considerable amounts of time.

SUMMARY

In general, the disclosure describes devices, systems, and techniques for actively cooling tissue near an implantable medical device (IMD) to a temperature below body temperature. For example, during a recharge session in which energy is transferred from an external charger to the battery of an IMD, the system may actively cool the skin to allow for higher recharge power and higher energy transfer rates that achieve faster recharge of the battery of the IMD. The system may cool a region of tissue and skin between the IMD and an external charger to a temperature below a normal surface skin temperature during wireless inductive coupling between a primary coil of the external charger and a secondary coil of the IMD. In some examples, the system may receive feedback from the patient and, in response to the feedback, adjust the cooling of the region of tissue and skin.

In one example, this disclosure describes a method including: charging, by an inductive charger, a rechargeable battery of an implantable medical device (IMD) within a patient, wherein the IMD comprises a housing that houses the rechargeable battery, and wherein a primary coil of the inductive charger is positioned above a region of skin of the patient proximate to the IMD; and cooling, by a heat exchanger, the region of skin below a normal ambient surface temperature of the region of skin, wherein an element of the heat exchanger is interposed between the primary coil and the region of skin.

In another example, this disclosure describes a system including: an implantable medical device (IMD) implantable within a surgical pocket of a patient, comprising: a housing; and a rechargeable battery within the housing; an inductive charger configured to charge the rechargeable battery of the IMD, wherein the inductive charger comprises a primary coil configured to be positioned above a region of skin of the patient proximate to the IMD; an element of a heat exchanger configured to be interposed between the primary coil and the region of skin; and one or more processors configured to control the heat exchanger to cool the region of skin below a normal ambient surface temperature of the region of skin.

In another example, this disclosure describes a system including: an implantable medical device (IMD) implantable within a surgical pocket of a patient, comprising: a housing; and a rechargeable battery within the housing; means for charging the rechargeable battery of the IMD positioned above a region of skin of the patient proximate to the IMD; means for cooling skin between the means for charging and the IMD; and one or more processors configured to control the means for cooling the skin to cool the skin between the means for charging and the IMD below a normal ambient surface temperature of the skin between the means for charging and the IMD.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
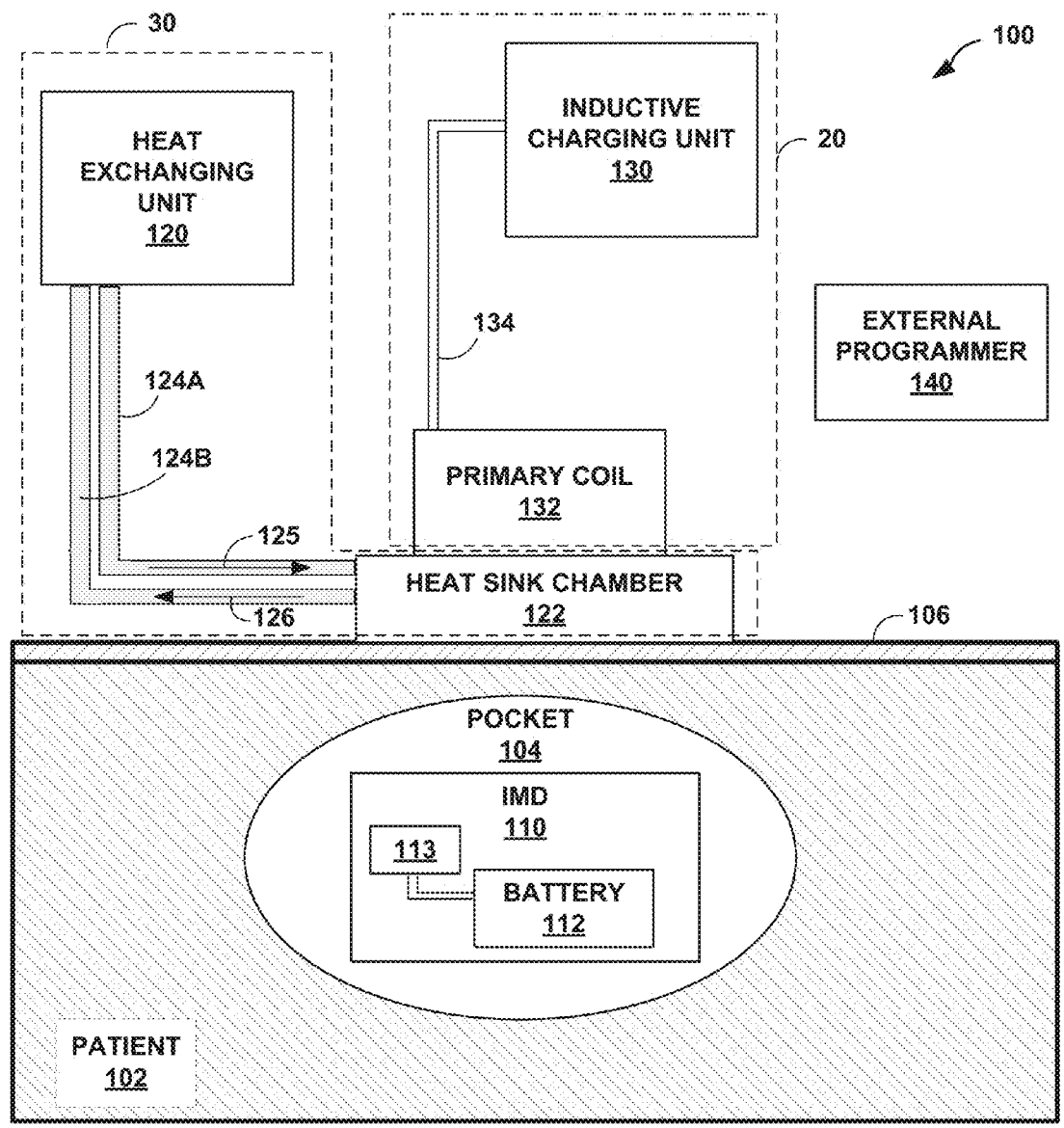
FIG. 1 is a block diagram depicting an example system for recharging an IMD according to the techniques of the disclosure.

As described herein, devices, systems, and techniques may provide active cooling of tissue near an implantable medical device (IMD) during recharging sessions in order to achieve higher energy transfer rates and shorter recharge times for the battery of the IMD. In one example, an IMD monitors one or more physiological parameters of a patient. In another example, the IMD generates and delivers electrical signals (e.g., pulses) to a target tissue that may include one or more nerves or muscle fibers of a patient. In yet another example, the IMD stimulates a target tissue that may include one or more nerves or muscle fibers of a patient via optical (e.g., light) or mechanical stimulation. In some examples, the IMD additionally or alternatively delivers drug therapy intravenously to the patient.

A therapy delivery system typically includes an implantable device for monitoring one or more physiological parameters of the patient and/or delivering therapy and an external programmer device for configuring and controlling the IMD. In one example, the IMD determines therapy parameters that define the therapy to be administered. In another example, the IMD relies on the external programmer to determine therapy parameters that define the therapy.

In one example, the IMD wirelessly uploads therapy and patient data to a remote workstation or network for review by a clinician. In another example, the IMD transmits therapy and patient data to the programmer. The programmer may in turn provide this data to another computer device or a user interface for review by a clinician. The programmer may be configured in two types: a clinician programmer, which allows the clinician access to a full set of features such as tests, diagnostics, configuration, and calibration of the IMD, and a patient programmer, which provides a limited feature set (e.g., minor adjustments to therapy or turning therapy on and off) for the patient as compared to the clinician programmer.

In some examples, a clinician implants the IMD into a pocket of tissue surgically created within the body. Because the IMD is implanted and may draw power from internal batteries, it is impractical to remove the IMD to replace or recharge the batteries when their electrical charge has been depleted. Accordingly, in some examples, a wireless, transcutaneous charging device recharges the batteries of many IMDs. Some methods of wireless power transfer may include magnetic inductive charging. In inductive coupling, an induction charger sends an alternating current through a primary coil of an inductor that in turn generates a magnetic field. This magnetic field may induce an electrical current in a secondary coil within the IMD, and recharge circuitry in the IMD uses the induced electrical current to recharge the battery of the IMD. Thus, the induction charger may recharge the battery of the IMD by wirelessly transmitting power across the primary and secondary coils of an inductor.

Inductive chargers suffer two challenges. First, the strength of a magnetic field decreases rapidly as the distance between the primary and secondary coils (i.e., the distance between the induction charger and the IMD) increases. Thus, a clinician may be tasked with positioning the primary coil of the induction charger as closely to the secondary coil of the IMD as possible. In other words, to function effectively, a clinician may position the primary coil typically against the skin of the patient in the region directly above the IMD to align the primary coil and the secondary coil for increased coupling efficiency. Second, the system generates heat as a result of the power transfer. For example, current from the induction charger generates resistive heating of the primary coil of the charger, the resulting magnetic field induces eddy currents within circuits and materials of the IMD that cause resistive heating of the IMD, the electrical current charging the battery causes resistive heating of the circuitry and battery of the IMD, and the magnetic field may directly heat the patient's tissue. These challenges may limit the recharging performance of the system. For example, to avoid undesirable heating of patient tissue during a recharge session, the system may need to limit the recharge power (e.g., the strength of the magnetic field) and/or limit the length of recharge sessions. Such limitations may result in longer and/or more frequent recharge sessions.

Although the system may be capable of quickly charging a battery through induction charging at high power levels (i.e., on the order of tens of minutes or less), IMD induction rechargers may be limited by the amount of heating the recharges cause in the tissue of the patient. In some systems, the inductive charger may recharge the IMD at a very slow and constant rate to keep the system in thermal equilibrium and prevent the primary coil or IMD from heating to a level that may be harmful to the patient. These systems can require up to four hours to fully recharge the battery of the IMD and are very inconvenient to a patient. Other systems have introduced a "boost" technique to reduce the amount of time required to recharge the device. According to the "boost" technique, the induction charger operates at its highest power level for a short period of time and is throttled down once temperatures of the system and/or patient exceed a threshold. These techniques may still require a significant amount of time to fully recharge the battery of an IMD due to the heat that is generating during the recharge session. Some systems may thus be limited to power transfer rates (e.g., a predetermined number of milliwatts (mW)) in some examples in order to prevent undesirable temperatures generated during recharge.

The recharge time of these systems may be limited by the amount of heat induced into the body by the induction charger. After a certain time, the induction charger of other devices must be switched off to allow built-up heat in the tissue of the patient to be dispersed by the body. Some systems attempt to increase the time at which the induction charger may operate at its highest power level by removing the heat generated by the charging operation before it reaches the tissue of the patient. For example, some systems surround the induction charger with phase-changing material. When the phase-change material is exposed to heat, it changes phases, efficiently absorbing the heat and preventing the heat from being absorbed by the tissue of the patient. However, phase-changing materials can only absorb a limited amount of energy, and once the phase-changing material become saturated, it may no longer function to draw heat from the body. Further, these devices function only to reduce or remove built-up heat from the surface of the body and the induction charger. Such devices do not cool the tissue of the patient below its natural temperature at equilibrium, nor do they attempt to cool the IMD and surgical pocket within the patient.

According to the techniques of the disclosure, a system includes a heat exchanger or other device that actively cools an IMD implanted within a patient during a battery recharge session by actively cooling the skin and surrounding tissue of the patient. For example, a heat exchanger may be interposed between the external primary coil of the inductive charger and the skin of the patient. The heat exchanger may actively cool the skin of the patient during the recharging process. It is observed that cooling the skin below its normal surface temperature has an unexpected effect of allowing the system to provide high rates of energy transfer for extended periods of time during recharge without heating tissue. The techniques of the disclosure may allow for recharging an IMD at higher power transfer rates, such as rates of at least 2800 mW. Thus, a system providing active cooling according to the techniques of the disclosure may allow an inductive recharger to recharge the battery of the IMD at its maximum recharging rate without inducing undesirable heating of the tissue of the patient.

FIG. 1 is a block diagram depicting an example system for recharging battery 112 of an IMD 110 according to the techniques of the disclosure. In one example, system 100 may include rechargeable IMD 110, a charging device 20, and a heat exchanger 30. System 100 may also include external programmer 140. As shown in FIG. 1, IMD 110 may be implanted into a pocket 104 of tissue within patient 102. Pocket 104 may be created surgically when IMD 110 is inserted into patient 102. In some examples, IMD 110 may be remotely controlled or configured by an external programmer 140. In some examples, external programmer 140 may come in clinician and patient programmer variants. The patient programmer variant of external programmer 140 may allow a patient to control basic features of IMD 110, such as selecting one of a plurality of therapy programs. In contrast, the clinician programmer variant of external programmer 140 may allow a clinician to configure various aspects of IMD 110, such as the amount of therapeutic drugs delivered, specific parameters of electrical stimulation therapy, or download data recorded by IMD 110. In other examples, two or more of heat exchanging unit 30, inductive charging unit 130, and external programmer 140 may be combined as a single device instead of separate devices as shown in FIG. 1.

In some examples, IMD 110 and external programmer 140 may each include one or more processors and memory. In some examples, the one or more processors may take the form of microprocessors, digital signal processors (DSPs), application specific integrated circuits (ASICs), field programmable gate arrays (FPGAs), or any other equivalent integrated or discrete logic circuitry, as well as any combinations of such components. In some examples, the memory may include random access memory (RAM), read only memory (ROM), programmable read only memory (PROM), erasable programmable read only memory (EPROM), electronically erasable programmable read only memory (EEPROM), flash memory, including executable instructions for causing the one or more processors to perform the actions attributed to them. Further, the memory may be implemented entirely in hardware, software, or a combination thereof.

IMD 110 may be an IMD configured to monitor one or more physiological parameters of patient 102, deliver electrical, mechanical, or optical stimulation to a patient 102, deliver drug therapy to a patient 102, or provide any other type of therapy. IMD 110 may include a rechargeable battery 112. In one example, battery 112 is a lithium battery. In other examples, battery 112 may be an alkaline battery, Nickel-Zinc battery, Nickel-metal hydride battery, Nickel-Cadmium battery, or any other type of device capable of receiving and storing an electrical charge and suitable for use within a medical device.

Battery 112 of IMD 110 may be wirelessly recharged by an inductive charger. In some examples, the inductive charger may include an inductive charging unit 130. Inductive charging unit 130 may transmit an alternating current signal along cable 134 to primary coil 132. However, in some examples where inductive charging unit 130 is a wireless recharger, cable 134 is omitted. In some examples, primary coil 132 is an inductor. The alternating current may induce a magnetic field when flowing through primary coil 132. This magnetic field may induce a current within secondary coil 113. The induced current may then recharge battery 112.

The charging process described above may generate heat in both primary coil 132 and IMD 110 due to resistive heating and induced eddy currents and directly produce electromagnetic heating of body tissue. In some examples, electric current flowing through primary coil 132 produces heat in primary coil 132. In other examples, IMD 110 may have a metallic case or structure in which the magnetic field may induce eddy currents in the metallic case. These eddy currents may also generate heat through resistive heating. Electrical currents generated in secondary coil 113, recharge circuitry, and battery 112 may also generate heat in IMD 110. In addition, a portion of the electromagnetic energy may interact with tissue of the patient and produce heating in the body tissue surrounding the IMD. Electromagnetic heating may be more substantial with higher frequencies of the electromagnetic radiation generated by primary coil 132. Together, these and other heating effects may cause the temperature of IMD 110 and pocket 104 to rise in temperatures during a battery recharge session. In some examples, and if not controlled, tissue may be heated above 39 degrees Celsius or even 43 degrees Celsius, which may cause damage to the patient tissue over a period of time. Accordingly, a cooling mechanism according to the present disclosure allows the pocket temperature of patient 102 to remain close to its normal temperature even during the recharge process. Such a cooling mechanism may reduce the propensity of the tissue of patient 102 to injury during the recharge process.

The heating of the tissue by IMD 110 may occur at different rates for different patients. For example, the rate of heating of tissue of a patient 102 may be affected by the type of tissue (e.g., cardiac, neural, etc.), the tissue density or specific heat capacity, the vascularization of the tissue, the depth of the tissue, and many other factors. Furthermore, the rate of heating of tissue may be affected by external conditions, such as ambient temperature or humidity. In some examples, the rate of heating of tissue may be due to the inherent sensitivity of the tissue of patient 102 to temperature variation.

According to the techniques of the disclosure, a heat exchanger 30 may be interposed between primary coil 132 and the region of skin 106 directly above IMD 110. In some examples, the heat exchanger 30 may operate according to a Peltier effect. For example, a Peltier heat pump may be used, wherein, when electrical current passes through the junction of two dissimilar conductors, heat is removed from the junction, causing a cooling effect. In other examples, the heat exchanger 30 may operate similar to a desktop pc-type water cooler. However, the techniques of the disclosure may be implemented with any variety of cooling system that is capable of actively cooling the surface of the skin of the patient below a desired threshold temperature.

In the example of FIG. 1, the heat exchanger 30 includes a heat exchanging unit 120, tubing 124A and 124B, and a heat sink chamber 122. The heat exchanger 30 operates by cycling a coolant from heat exchanging unit 120, through tubing 124A along path 125 into heat sink chamber 122, and back through tubing 124B along path 125 to heat exchanging unit 120. The coolant within heat sink chamber 122 absorbs heat from primary coil 132 and skin 106, causing primary coil 132 and skin 106 to decrease in temperature while the coolant within heat sink chamber 122 increases in temperature. The heated coolant flows back through tubing 124B to heat exchanging unit 120, where it is re-cooled and recirculated to heat sink chamber 122. In some examples, the coolant is re-cooled by flowing air across the fluid, moving the heat into the surrounding air. In some examples, the coolant may be water, ethanol, propylene glycol, ammonia, or any other fluid suitable for use as a coolant. In some examples, the coolant may be selected for its non-toxic properties and suitability for use in a medical device. In some examples, the coolant may be compressed and then expanded to assist in the cooling process.

In some examples, a sheath of outer tubing encapsulates inner tubing 124A and 124B. In this example, inner tubing 124A and 124B carry fresh and heated coolant, respectively. Further, the sheath of outer tubing provides structural support and protection to inner tubing 124A and 124B.

In some examples, heat exchanging unit 120 may cool the skin to a temperature range below the normal ambient surface temperature of the skin (e.g., approximately 28 to 32 degrees Celsius). For example, heat exchanging unit 120 may cool the skin below approximately 25 degrees Celsius in some examples, and below approximately 22 degrees Celsius in other examples. Further, in any of the foregoing examples, heat exchanging unit 120 may keep the temperature of the skin above a certain minimum temperature. For example, heat exchanging unit 120 may keep the skin above approximately 5 degrees in some examples, above approximately 15 degrees in other examples, and above approximately 18 degrees in still other examples. In some examples, heat exchanging unit 120 may cool the skin to a temperature between approximately 5 degrees Celsius and 25 degrees Celsius. In other examples, heat exchanging unit 120 may cool the skin to a temperature greater than approximately 15 degrees Celsius and less than approximately 25 degrees Celsius. In other examples, heat exchanging unit 120 may cool the skin to a temperature greater than approximately 15 degrees Celsius and less than 22 degrees Celsius. In still other examples, heat exchanging unit 120 may cool the skin to a temperature greater than approximately 18 degrees Celsius and less than 22 degrees Celsius. In another example, heat exchanging unit 120 may cool the skin to a temperature between approximately 18 degrees Celsius and approximately 25 degrees Celsius.

The foregoing example temperatures may be appropriate for an IMD implanted approximately 3 centimeters (cm) from the surface of the skin. These lower temperatures may allow inductive charging unit 130 to generate full power during a recharge session without damaging skin 106 or any other tissue of the patient. The desired skin temperature may also be determined based on the thickness and/or tissue type between the primary coil 132 and IMD 110. For example, the skin may need to be maintained at a colder temperature for an IMD implanted further from the surface of the skin than an IMD implanted closer to the surface of the skin. A patient may experience discomfort if the skin of the patient is suddenly exposed to a cold temperature. Accordingly, in some examples, heat exchanging unit 120 may slowly ramp the temperature of the skin down from its normal ambient temperature to a desired cooler temperature (e.g., reducing the temperature of the skin by a certain number of degrees per minute such as 1 degree or 3 degrees per minute from 28 degrees Celsius to 18 degrees Celsius) to prevent discomfort to the patient. The ramp may be linear, stepped, exponential, or any other type of ramp. For example, the ramp may be initially steep and gradually reduce the rate of temperature change as the skin becomes colder.

In some examples, heat exchange unit 120 (or other device such as external programmer 140 or inductive charging unit 130) may receive feedback from the patient and, in response to the feedback, adjust the cooling of the region of tissue and skin. For example, heat exchange unit 120 may receive user input indicating that the chilling process is too fast (e.g., the temperature is getting too cold too fast) or too slow (e.g., the temperature is not getting cold enough or is remaining too warm) and change the cooling ramp in response to receiving the user input. In other examples, heat exchange unit 120 may receive user input indicating that the skin of the patient is too cold, and in response to the user input, heat exchange unit 120 adjusts the temperature range (e.g., adjusting the cooling temperature range from 15-25 degrees Celsius to 18-25 degrees Celsius. In other examples, heat exchange unit 120 receive user input indicating that the skin of the patient is too warm, and in response to the user input, heat exchange unit 120 adjusts the cooling temperature range (e.g., adjusting the cooling temperature range from 15-25 degrees Celsius to 15-22 degrees Celsius). In any of the foregoing examples, in response to the user input, heat exchange unit 120 may adjust one or both of a minimum of the cooling temperature range or a maximum of the cooling temperature range.

The architecture of system 100 illustrated in FIG. 1 is shown for exemplary purposes only. The techniques as set forth in this disclosure may be implemented in the example system of FIG. 1, as well as other types of systems not described specifically herein. In some examples, external programmer 140 may be used to control the rate of recharging performed by inductive charting unit 130. In other examples, external programmer 140 may be used to control the amount of cooling performed by heat exchanging unit 120. In some examples, external programmer 140 may control the amount of cooling by altering the rate of coolant flow through heat sink chamber 122 or by altering the temperature of the coolant. In further examples, the amount of cooling performed by heat exchanging unit 120 may be controlled by IMD 110, by inductive charging unit 130, or by one or more processors within heat exchanging unit 120. In other examples, one or more of these devices may provide the functionality of two or more of the devices described in FIG. 1. Nothing in this disclosure should be construed so as to limit the techniques of this disclosure to the example system illustrated by FIG. 1.

Accordingly, it may be seen that a system according to the techniques of the disclosure may allow for active cooling of the skin of a patient. By actively cooling the skin of the patient, the primary coil of an inductive charger and the surgical pocket within which an IMD is implanted may be maintained at a temperature well below that which may induce undesirable heating of the tissue of the patient.

Thus, a system according to the techniques of the disclosure may allow for the inductive charging of an IMD at a rate much higher than other systems because the heat generated by fast rates of recharge is removed from the system before it can accumulate to undesirable levels and risk harm to the tissue of the patient. Accordingly, the system of the present disclosure may allow for much higher energy transfer rates of charging than other systems in which active cooling is not provided.

Figure 2:
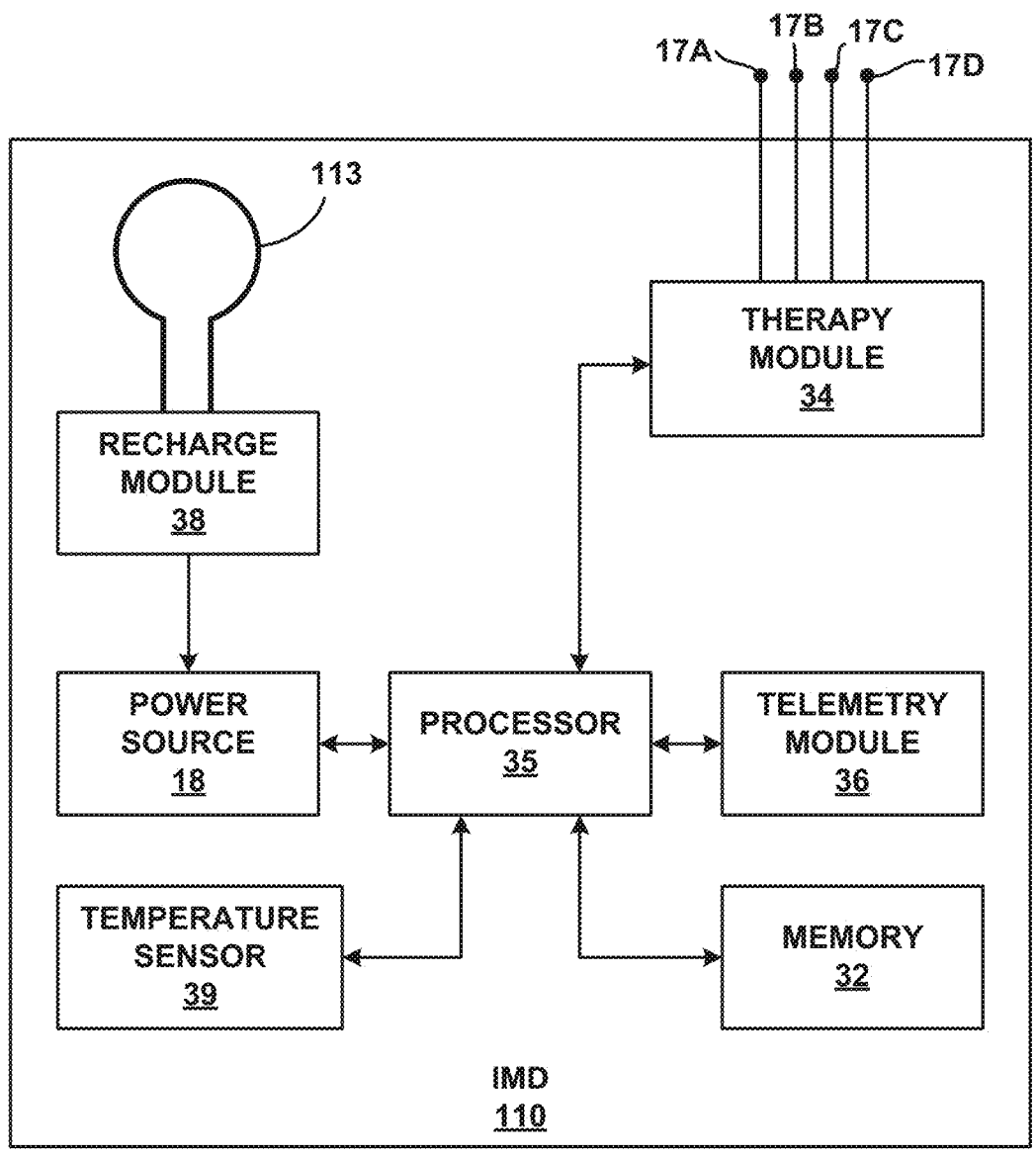
FIG. 2 is a block diagram depicting an example IMD according to the techniques of the disclosure.

FIG. 2 is a block diagram of the example IMD 110 of FIG. 1 for delivering deep brain stimulation therapy. In the example of FIG. 2, IMD 110 includes temperature sensor 39, coil 113, processor 35, therapy module 34, recharge module 38, memory 32, telemetry module 36, and rechargeable power source 18. In other examples, IMD 110 may include a greater or fewer number of components. In some examples, such as where the tissue temperature is calculated from the transmitted power, IMD 110 may not include temperature sensor 39.

In general, IMD 110 may comprise any suitable arrangement of hardware, alone or in combination with software and/or firmware, to perform the various techniques described herein attributed to IMD 110 and processor 35. In various examples, IMD 110 may include one or more processors 35, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 110 also, in various examples, may include a memory 32, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor 35, therapy module 34, recharge module 38, and telemetry module 36 are described as separate modules, in some examples, processor 35, therapy module 34, recharge module 38, and telemetry module 36 are functionally integrated. In some examples, processor 35, therapy module 34, recharge module 38, and telemetry module 36 correspond to individual hardware units and/or include circuitry such as, such as ASICs, DSPs, FPGAs, or other electrical circuitry and/or hardware units.

Memory 32 may store therapy programs or other instructions that specify therapy parameter values for the therapy provided by therapy module 34 and IMD 110. In some examples, memory 32 may also store temperature data from temperature sensor 39, instructions for recharging rechargeable power source 18, circuit models, open-circuit voltage models, tissue models, thresholds, instructions for communication between IMD 110 and charging device 20, or any other instructions required to perform tasks attributed to IMD 110. In this manner, memory 32 may be configured to store a tissue model such that processor 35 may be configured to calculate tissue temperature surrounding IMD 110 based on the tissue model and the power received by secondary coil 113 and rechargeable power source 18 over a period of time. In some examples, memory 32 may be configured to store data representative of an energy absorption tissue model used by processor 35 to determine the energy absorption of tissue at a particular operating frequency. In some examples, memory 32 may be configured to store an open-circuit voltage lookup table with data representative of open-circuit voltage of power source 18 at a particular state-of-charge (SOC). The open-circuit voltages of the lookup table may, in some examples, also be based on the age of the battery 112 of power source 18 or other factors that may affect the open-circuit voltage. In these examples, processor 35 may use the open-circuit voltage lookup table to determine the open-circuit voltage, the effective power delivered to power source 18, and the resistive heat loss from power source 18 at any given SOC of power source 18. In some examples, memory 32 may also be configured to store data of a Thevenin equivalent circuit that is modeled on power source 18.

Generally, therapy module 34 may generate and deliver electrical stimulation under the control of processor 35. In some examples, processor 35 controls therapy module 34 by accessing memory 32 to selectively access and load at least one of the stimulation programs to therapy module 34. For example, in operation, processor 35 may access memory 32 to load one of the stimulation programs to therapy module 34. In such examples, relevant stimulation parameters may include a voltage amplitude, a current amplitude, a pulse rate, a pulse width, a duty cycle, a pulse pattern for non-regular stimulation, a waveform for non-pulsed stimulation or the combination of electrodes 17A, 17B, 17C, and 17D that therapy module 34 uses to deliver the electrical stimulation signal. Although therapy module 34 may be configured to generate and deliver electrical stimulation therapy via one or more of electrodes 17A, 17B, 17C, and 17D, therapy module 34 may be configured to provide different therapy to patient 102. For example, instead of the four electrodes 17A-17D of FIG. 2, therapy module 34 may have any number of electrodes (e.g., fewer than four or greater than four). As a further example, therapy module 34 may be configured to deliver drug delivery therapy via a catheter. These and other therapies may be provided by IMD 110.

IMD also includes components to receive power from charging device 20 to recharge rechargeable power source 18 when rechargeable power source 18 has been at least partially depleted. As shown in FIG. 2, IMD 110 includes secondary coil 113 and recharge module 38 coupled to rechargeable power source 18. Recharge module 38 may be configured to charge rechargeable power source 18 with the selected power level determined by either processor 35 or charging device 20. Although processor 35 may provide some commands to recharge module 38 in some examples, processor 35 may not need to control any aspect of recharging.

Secondary coil 113 may include a coil of wire or other arrangement capable of inductive coupling with a primary coil disposed external to patient 102. Although primary coil 132 is illustrated as a simple loop of in FIG. 3, primary coil 132 may include multiple turns of wire. Secondary coil may include a winding of wire comprising one or more turns of wire configured such that an electrical current can be induced within secondary coil 113 from a magnetic field. The induced electrical current may then be used to recharge rechargeable power source 18. In this manner, the electrical current may be induced in secondary coil 113 associated with rechargeable power source 18. The induction may be caused by electrical current generated in the primary coil of charging device 20 and based on the selected power level. The coupling between secondary coil 113 and the primary coil of charging device 20 may be dependent upon the alignment of the two coils. Generally, the coupling efficiency increases when the two coils are closely aligned axially and are in close proximity to each other. Charging device 20 and/or IMD 110 may provide one or more audible tones or visual indications of the alignment.

Although inductive coupling is generally described as the method for recharging rechargeable power source 18, other wireless energy transfer techniques may alternatively be used. Any of these techniques may generate heat in IMD 110 such that the charging process can be controlled using the calculated estimated energy transfer as feedback. As another example, processor 35 may use the temperature and current state of a battery of power source 18 as feedback for controlling the charging process.

Recharge module 38 may include one or more circuits that filter and/or transform the electrical signal induced in secondary coil to an electrical signal capable of recharging rechargeable power source 18. For example, in alternating current induction, recharge module 38 may include a half-wave rectifier circuit and/or a full-wave rectifier circuit configured to convert alternating current from the induction to a direct current for rechargeable power source 18. The full-wave rectifier circuit may be more efficient at converting the induced energy for rechargeable power source 18. However, a half-wave rectifier circuit may be used to store energy in rechargeable power source 18 at a slower rate. In some examples, recharge module 38 may include both a full-wave rectifier circuit and a half-wave rectifier circuit such that recharge module 38 may switch between each circuit to control the charging rate of rechargeable power source 18 and temperature of IMD 110.

In some examples, recharge module 38 may include a measurement circuit configured to measure the current and/or voltage induced during inductive coupling. This measurement may be used to measure or calculate the power transmitted to power source 18 of IMD 110 from charging device 20. In some examples, the transmitted power may be used to calculate the estimated energy transfer, which may be used to approximate the temperature of IMD 110 and that of the surrounding tissue. This method may be used to indirectly measure the temperature of tissue in contact with the housing of IMD 110. In some examples, recharge module 38 or other module may include an electrometer, voltmeter, or ammeter, which may measure the charge current being applied to rechargeable power source 18 and communicate this charge current to processor 35.

Rechargeable power source 18 may include one or more capacitors, batteries, and/or other energy storage devices. Rechargeable power source 18 may then deliver operating power to the components of IMD 110. In some examples, rechargeable power source 18 may include a power generation circuit to produce the operating power. Rechargeable power source 18 may be configured to operate through hundreds or thousands of discharge and recharge cycles. Rechargeable power source 18 may also be configured to provide operational power to IMD 110 during the recharge process. In some examples, rechargeable power source 18 may be constructed with materials to reduce the amount of heat generated during charging. In other examples, IMD 110 may be constructed of materials that may help dissipate generated heat at rechargeable power source 18, recharge module 38, and/or secondary coil 113 over a larger surface area of the housing of IMD 110.

Although rechargeable power source 18, recharge module 38, and secondary coil 113 are shown as contained within the housing of IMD 110, at least one of these components may be disposed outside of the housing. For example, secondary coil 113 may be disposed outside of the housing of IMD 110 to facilitate better coupling between secondary coil 113 and the primary coil of charging device 20. These different configurations of IMD 110 components may allow IMD 110 to be implanted in different anatomical spaces or facilitate better inductive coupling alignment between the primary and secondary coils.

IMD 110 may also include temperature sensor 39. Temperature sensor 39 may include one or more temperature sensors (e.g., thermocouples or thermistors) configured to measure the temperature of IMD 110. Temperature sensor 39 may be disposed internal of the housing of IMD 110, contacting the housing, formed as a part of the housing, or disposed external of the housing. As described herein, temperature sensor 39 may be used to directly measure the temperature of IMD 110 and/or tissue surrounding and/or contacting the housing of IMD 110. Processor 30, or charging device 20, may use this temperature measurement as tissue temperature feedback to determine the estimated energy transfer provided to tissue during charging of rechargeable power source 18. Although a single temperature sensor may be adequate, multiple temperature sensors may provide a better temperature gradient or average temperature of IMD 110. The various temperatures of IMD 110 may also be modeled and provided to determine the estimated energy transfer to tissue of patient 12. Although processor 30 may continually measure temperature using temperature sensor 39, processor 30 may conserve energy by only measuring temperature during recharge sessions. Further, temperature may be sampled at a rate necessary to calculate the estimated energy transfer, but the sampling rate may be reduced to conserve power as appropriate.

Processor 35 may also control the exchange of information with charging device 20 and/or an external programmer using telemetry module 36. Telemetry module 36 may be configured for wireless communication using radio frequency protocols or inductive communication protocols. Telemetry module 36 may include one or more antennas configured to communicate with charging device 20, for example. Processor 35 may transmit operational information and receive therapy programs or therapy parameter adjustments via telemetry module 36. Also, in some examples, IMD 110 may communicate with other implantable devices, such as stimulators, control devices, or sensors, via telemetry module 36. In addition, telemetry module 36 may be configured to transmit the measured tissue temperatures from temperature sensor 39, the determined resistive heat loss from power source 18, and/or the determined energy absorbed by tissue of patient 102, for example. In some examples, tissue temperature may be measured adjacent to rechargeable power source 18. In this manner, charging device 20 may compare the estimated energy transfer with the transmitted tissue temperature. In other examples, processor 35 may calculate the estimated energy transfer and transmit the calculated estimated energy transfer using telemetry module 36.

In other examples, processor 35 may transmit additional information to charging device 20 related to the operation of rechargeable power source 18. For example, processor 35 may use telemetry module 36 to transmit indications that rechargeable power source 18 is completely charged, rechargeable power source 18 is fully discharged, how much charge (e.g., the charge current) is being applied to rechargeable power source 18, the charge capacity of rechargeable power source 18, the state-of-charge (SOC) of rechargeable power source 18, or any other charge information of rechargeable power source 18. Processor 35 may also transmit information to charging device 20 that indicates any problems or errors with rechargeable power source 18 that may prevent rechargeable power source 18 from providing operational power to the components of IMD 110.

The architecture of IMD 110 illustrated in FIG. 2 is shown as an example. The techniques as set forth in this disclosure may be implemented in the example IMD 110 of FIG. 2, as well as other types of systems not described specifically herein. Nothing in this disclosure should be construed so as to limit the techniques of this disclosure to the example architecture illustrated by FIG. 2.

Figure 3:
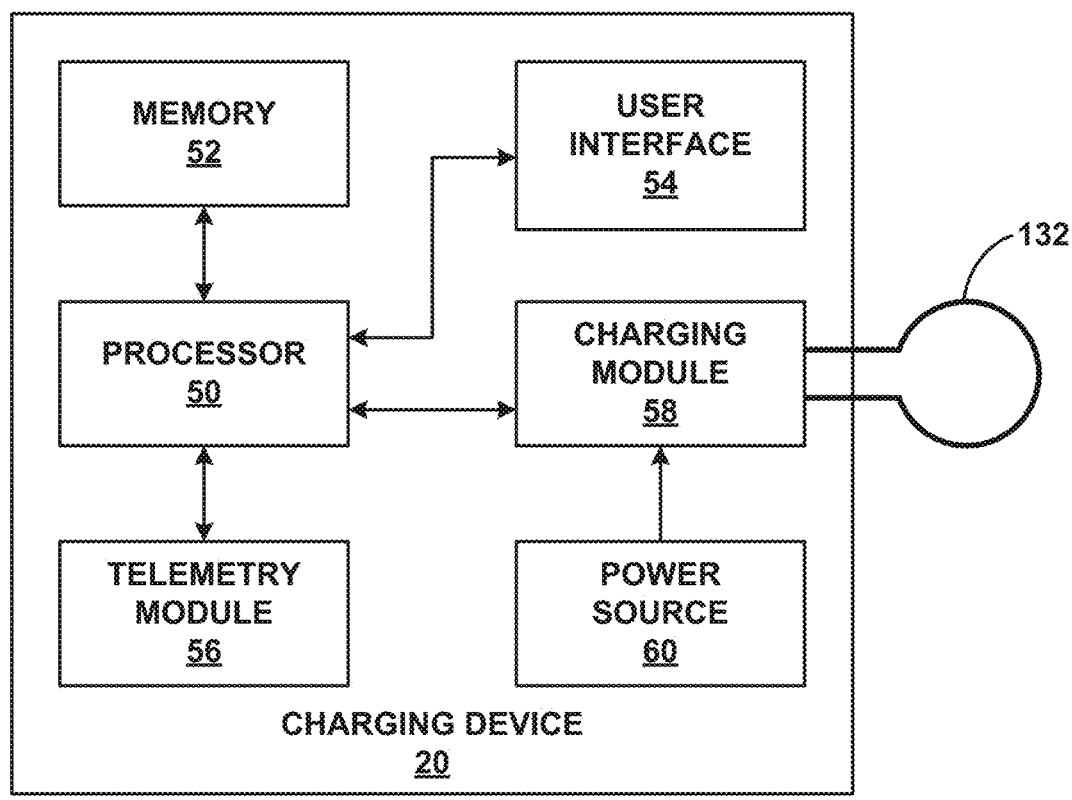
FIG. 3 is a block diagram depicting an example inductive recharger according to the techniques of the disclosure.

FIG. 3 is a block diagram depicting an example inductive recharger according to the techniques of the disclosure. While charging device 20 may generally be described as a hand-held device, charging device 20 may be a larger portable device or a more stationary device. In addition, in other examples, charging device 20 may be included as part of an external programmer or include functionality of an external programmer. In addition, charging device 20 may be configured to communicate with an external programmer. As illustrated in FIG. 3, charging device 20 may include a processor 50, memory 52, user interface 54, telemetry module 56, power module 58, coil 132, and power source 60. Memory 52 may store instructions that, when executed by processor 50, cause processor 50 and external charging device 20 to provide the functionality ascribed to external charging device 20 throughout this disclosure.

In general, charging device 20 comprises any suitable arrangement of hardware, alone or in combination with software and/or firmware, to perform the techniques attributed to charging device 20, and processor 50, user interface 54, telemetry module 56, and charging module 58 of charging device 20. In various examples, charging device 20 may include one or more processors, such as one or more microprocessors, DSPs, ASICs, FPGAs, or any other equivalent integrated or discrete logic circuitry, as well as any combinations of such components. Charging device 20 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processor 50 and telemetry module 56 are described as separate modules, in some examples, processor 50 and telemetry module 56 are functionally integrated. In some examples, processor 50 and telemetry module 56 and charging module 58 correspond to individual hardware units and/or electrical circuitry, such as ASICs, DSPs, FPGAs, or other hardware units.

Memory 52 may store instructions that, when executed by processor 50, cause processor 50 and charging device 20 to provide the functionality ascribed to charging device 20 throughout this disclosure. For example, memory 52 may include instructions that cause processor 50 to calculate estimated energy transfers, establish thresholds, select power levels based on the estimated energy transfers and otherwise control charging module 58, communicate with IMD 110, or instructions for any other functionality. In addition, memory 52 may include a record of selected power levels, calculated estimated energy transfers, or any other data related to charging rechargeable power source 18. Processor 50 may, when requested, transmit any of this stored data in memory 52 to another computing device for review or further processing.

In some examples, memory 52 may be configured to store an open-circuit voltage lookup table with data representative of open-circuit voltage of power source 18 at a particular state-of-charge (SOC), age of power source 18, and/or any other factors that may affect the open-circuit voltage. In these examples, processor 50 may use the open-circuit voltage lookup table to determine the open-circuit voltage and then use the open-circuit voltage to determine an estimated power stored in (e.g., an effective power delivered to) power source 18. This open-circuit voltage may be used to determine the resistive heat loss from power source 18 at any given SOC of power source 18. In some examples, memory 52 may also be configured to store data of a Thevenin equivalent circuit that is modeled on power source 18. In some examples, memory 52 may be configured to store data representative of an energy absorption tissue model used by processor 50 to determine the energy absorption of tissue at a particular operating frequency. In some examples, memory 52 may be configured to store data representative of a tissue model used by processor 50 to calculate tissue temperature based on tissue model and power transmitted to rechargeable power source 18 over a period of time. Tissue model may indicate how the temperature of tissue surrounding IMD 110 changes over time based on, i.e., as a function of, the estimated energy transfer. Therefore, processor 50 may be able to estimate tissue temperature without direct measurement of the temperature of tissue surrounding the housing of IMD 110.

User interface 54 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processor 50 may present and receive information relating to the charging of rechargeable power source 18 via user interface 54. For example, user interface 54 may indicate when charging is occurring, quality of the alignment between coils 113 and 132, the selected power level, current charge level of rechargeable power source 18, duration of the current recharge session, anticipated remaining time of the charging session, or any other information. Processor 50 may receive some of the information displayed on user interface 54 from IMD 110 in some examples.

User interface 54 may also receive user input via user interface 54. The input may be, for example, in the form of pressing a button on a keypad or selecting an icon from a touch screen. The input may request starting or stopping a recharge session, a desired level of charging, or one or more statistics related to charging rechargeable power source 18 (e.g., the estimated energy transfer). In this manner, user interface 54 may allow the user to view information related to the charging of rechargeable power source 18 and/or receive charging commands.

Charging device 20 also includes components to transmit power to recharge rechargeable power source 18 associated with IMD 110. As shown in FIG. 3, charging device 20 includes primary coil 132 and charging module 58 coupled to power source 60. Charging module 58 may be configured to generate an electrical current in primary coil 132 from voltage stored in power source 60. Although primary coil 132 is illustrated as a simple loop in FIG. 3, primary coil 132 may include multiple turns of wire. Charging module 58 may generate the electrical current according to a power level selected by processor 50 based on the estimated energy transfer. As described herein, processor 50 may select a high power level, low power level, or a variety of different power levels to control the rate of recharge in rechargeable power source 18 and the temperature of IMD 110. In some examples, processor 50 may control charging module 58 based on a power level selected by processor 35 of IMD 110.

Primary coil 132 may include a coil of wire, e.g., having multiple turns, or other device capable of inductive coupling with a secondary coil 113 disposed within patient 102. Primary coil 132 may include a winding of wire configured such that an electrical current generated within primary coil 132 can produce a magnetic field configured to induce an electrical current within secondary coil 113. Primary coil 132 may be constructed of certain dimensions and/or driven to produce electromagnetic energy of a particular frequency selected for secondary coil 113. The induced electrical current may then be used to recharge rechargeable power source 18. In this manner, the electrical current may be induced in secondary coil 113 associated with rechargeable power source 18. The coupling efficiency between secondary coil 113 and primary coil 132 of charging device 20 may be dependent upon the alignment of the two coils. Generally, the coupling efficiency increases when the two coils are closely aligned axially and are in close proximity to each other. User interface 54 of charging device 20 may provide one or more audible tones or visual indications of the alignment.

Charging module 58 may include one or more circuits that generate an electrical signal, and an electrical current, within primary coil 132. Charging module 58 may generate an alternating current of specified amplitude and frequency in some examples. In other examples, charging module 58 may generate a direct current. In any case, charging module 58 may be capable of generating electrical signals, and subsequent magnetic fields, to transmit various levels of power to IMD 110. In this manner charging module 58 may be configured to charge rechargeable power source 18 of IMD 110 with the selected power level.

The power level that charging module 58 selects for charging may be used to vary one or more parameters of the electrical signal generated for coil 132. For example, the selected power level may specify a wattage, electrical current of primary coil 132 or secondary coil 113, current amplitude, voltage amplitude, pulse rate, pulse width, duty cycle, or any other parameter that may be used to modulate the power transmitted from coil 132. In this manner, each power level may include a specific parameter set that specifies the signal for each power level. Changing from one power level to another power level, e.g., a high power level to a low power level, may include adjusting one or more parameters. The parameters of each power level may be selected based on hardware characteristics of charging device 20 and/or IMD 110.

Power source 60 may deliver operating power to the components of charging device 20. Power source 60 may also deliver the operating power to drive primary coil 132 during the charging process. Power source 60 may include a battery and a power generation circuit to produce the operating power. In some examples, the battery may be rechargeable to allow extended portable operation. In other examples, power source 60 may draw power from a wired voltage source such as a consumer or commercial power outlet.

Although power source 60 and charging module 58 are shown within a housing of charging device 20, and primary coil 132 is shown external to charging device 20 (as may be the case when primary coil is contained within an antenna coupled to charging device 20 by a cable), different configurations may also be used. For example, primary coil 132 may also be disposed within the housing of charging device 20. In another example, power source 60, charging module 58, and primary coil 132 may be all located external to the housing of charging device 20 and coupled to charging device 20.

Telemetry module 56 supports wireless communication between IMD 110 and charging device 20 under the control of processor 50. Telemetry module 56 may also be configured to communicate with another computing device via wireless communication techniques, or direct communication through a wired connection. In some examples, telemetry module 56 may be substantially similar to telemetry module 36 of IMD 110 described herein, providing wireless communication via an RF or proximal inductive medium. In some examples, telemetry module 56 may include an antenna, which may take on a variety of forms, such as an internal or external antenna.

Examples of local wireless communication techniques that may be employed to facilitate communication between charging device 20 and IMD 110 include RF communication according to the 802.11 or Bluetooth specification sets or other standard or proprietary telemetry protocols. In this manner, other external devices may be capable of communicating with charging device 20 without needing to establish a secure wireless connection. As described herein, telemetry module 56 may be configured to receive a measured tissue temperature, a determined resistive heat loss from power source 18, determined energy absorption of tissue of patient 102, a determined estimated energy transfer, and/or any other information relevant to determining, in real time, the estimated energy transfer from IMD 110 or the state of the energy transfer process.

In some examples, tissue temperature may be measured adjacent to rechargeable power source 18, such as near the housing of IMD 110 or external of the housing. Although IMD 110 may measure tissue temperature, one or more different implantable temperature sensors (e.g., standalone implantable temperature sensing devices) may independently measure tissue temperature at different positions and transmit the temperature to charging device 20. In some examples, multiple temperature readings by IMD 110 may be averaged or otherwise used to produce a single temperature value that is transmitted to charging device 20. The temperature may be sampled and/or transmitted at different rates, e.g., on the order of microseconds, milliseconds, seconds, minutes, or even hours.

Figure 4:
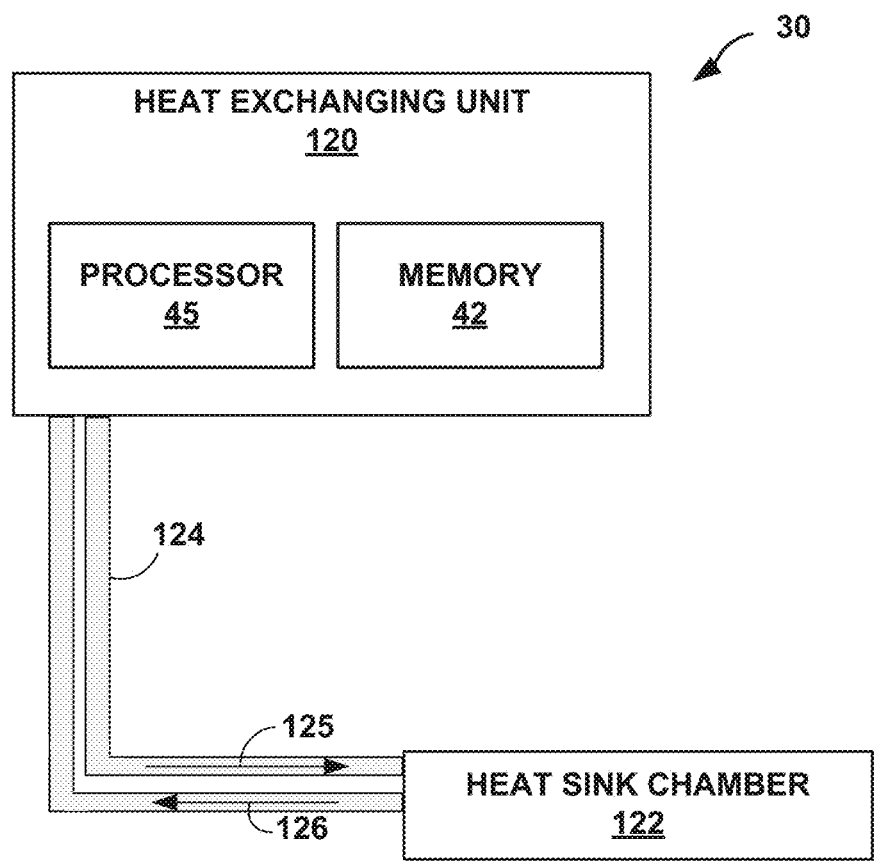
FIG. 4 is a block diagram depicting an example heat exchanger according to the techniques of the disclosure.

FIG. 4 is a block diagram depicting an example heat exchanger 30 according to the techniques of the disclosure. In the example of FIG. 4, the heat exchanger 30 includes a heat exchanging unit 120, tubing 124A-124B, and a heat sink chamber 122. The heat exchanger 30 operates by cycling a coolant from heat exchanging unit 120, through tubing 124A along path 125 into heat sink chamber 122, and back to heat exchanging unit 120 along path 126 through tubing 124B. The coolant within heat sink chamber 122 absorbs heat from primary coil 132 and skin 106, causing primary coil 132 and skin 106 to decrease in temperature while the coolant within heat sink chamber 122 increases in temperature. The heated coolant flows back through tubing 124B to heat exchanging unit 120, where it is re-cooled and recirculated to heat sink chamber 122. In some examples, the coolant is re-cooled by flowing air across the fluid, moving the heat into the surrounding air. In some examples, the coolant may be water, ethanol, propylene glycol, ammonia, or any other fluid suitable for use as a coolant. In some examples, the coolant may be selected for its non-toxic properties and suitability for use in a medical device. In some examples, the coolant may be compressed and then expanded to assist in the cooling process.

In general, heat exchanger 30 may comprise any suitable arrangement of hardware, alone or in combination with software and/or firmware, to perform the various techniques described herein attributed to heat exchanger 30. In various examples, heat exchanger 30 may include one or more processors 45, such as one or more microprocessors, digital signal processors (DSPs), application specific integrated circuits (ASICs), field programmable gate arrays (FPGAs), or any other equivalent integrated or discrete logic circuitry, as well as any combinations of such components. Heat exchanger 30 also, in various examples, may include a memory 42, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them.

Memory 42 may store programs or other instructions that specify cooling routines for the cooling operations provided by heat exchanger 30. In some examples, memory 42 may also store temperature data from one or more temperature sensors (e.g., temperature sensor 250E described below), instructions for heat exchanger 30, predetermined temperature ranges or temperature limits, or any other instructions required to perform tasks attributed to heat exchanger 30.

In some examples, heat exchanging unit 120 may cool the skin to a temperature range below the normal ambient surface temperature of the skin (e.g., approximately 28 to 32 degrees Celsius). For example, heat exchanging unit 120 may cool the skin below approximately 25 degrees Celsius in some examples, and below approximately 22 degrees Celsius in other examples. Further, in any of the foregoing examples, heat exchanging unit 120 may keep the temperature of the skin above a certain minimum temperature. For example, heat exchanging unit 120 may keep the skin above approximately 5 degrees in some examples, above approximately 15 degrees in other examples, and above approximately 18 degrees in still further examples. In some examples, heat exchanging unit 120 may cool the skin to a temperature greater than approximately 5 degrees Celsius and less than 25 degrees Celsius. In other examples, heat exchanging unit 120 may cool the skin to a temperature greater than approximately 15 degrees Celsius and less than 25 degrees Celsius. In other examples, heat exchanging unit 120 may cool the skin to a temperature greater than approximately 15 degrees Celsius and less than 22 degrees Celsius. In still other examples, heat exchanging unit 120 may cool the skin to a temperature greater than approximately 18 degrees Celsius and less than 22 degrees Celsius.

These example temperatures may be appropriate for an IMD implanted approximately 3 centimeters (cm) from the surface of the skin. These lower temperatures may allow inductive charging unit 130 to generate full power during a recharge session without damaging skin 106 or any other tissue of the patient. The desired skin temperature may also be determined based on the thickness and/or tissue type between the primary coil 132 and IMD 110. For example, the skin may need to be maintained at a colder temperature for an IMD implanted further from the surface of the skin than an IMD implanted closely to the surface of the skin. A patient may experience discomfort if the skin of the patient is suddenly exposed to a cold temperature. Accordingly, in some examples, heat exchanging unit 120 may slowly ramp the temperature of the skin down from its normal ambient temperature to a desired cooler temperature (e.g., reducing the temperature of the skin by a certain number of degrees per minute such as 1 degree or 3 degrees per minute from 28 degrees Celsius to 18 degrees Celsius) to prevent discomfort to the patient. The ramp may be linear, stepped, exponential, or any other type of ramp. For example, the ramp may be initially steep and gradually reduce the rate of temperature change as the skin becomes colder. In some examples, heat exchange unit 120 may receive user input indicating that the chilling process is too fast or too slow and change the cooling ramp in response to receiving the user input.

Figure 5:
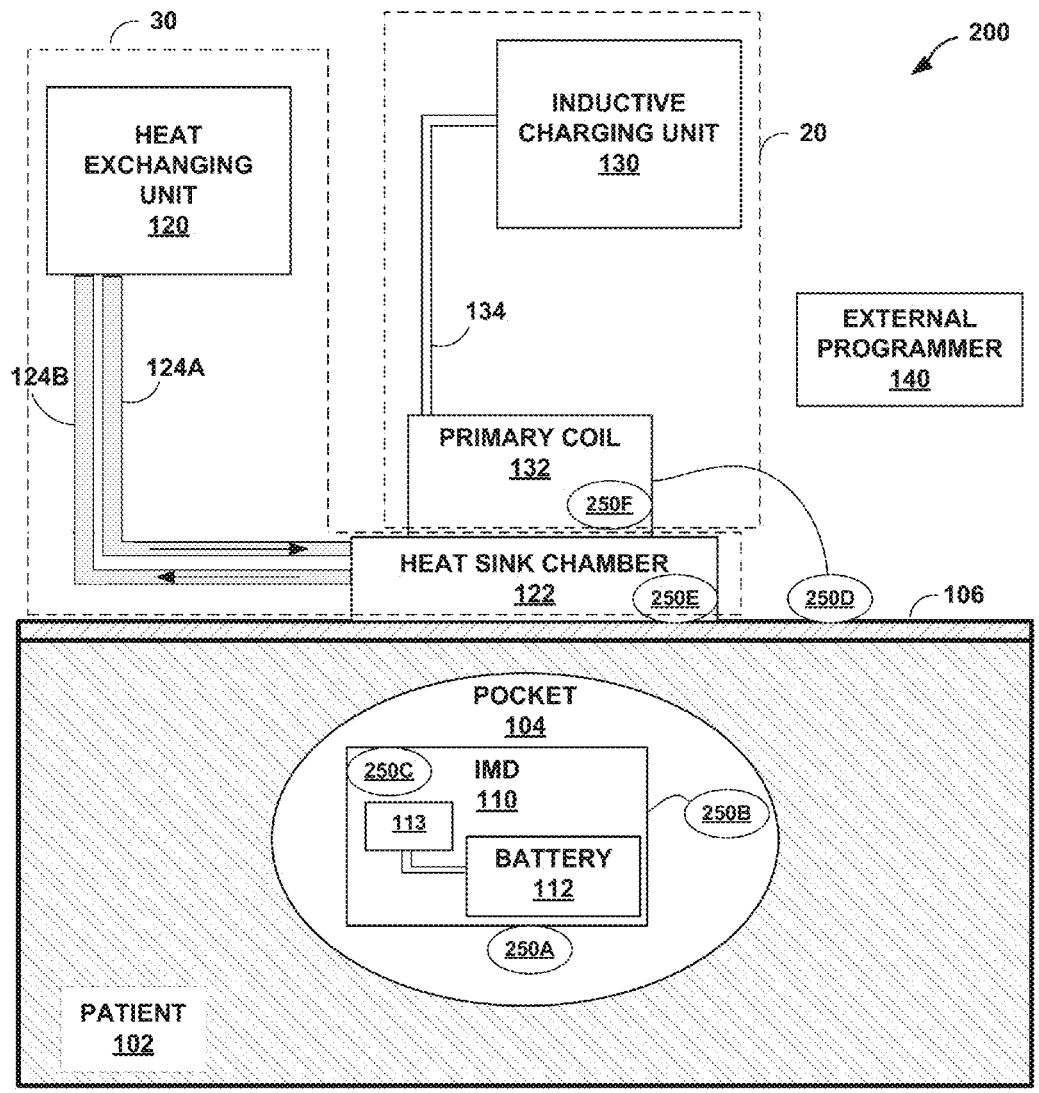
FIG. 5 is a block diagram depicting an example system for recharging an IMD according to the techniques of the disclosure.

FIG. 5 is a block diagram depicting an example system 200 for recharging IMD 110 according to the techniques of the disclosure. It will be understood that in FIG. 5, the depicted size and location of various components including the primary coil 132 and secondary coil 113 are not intended to necessarily convey actual size or relative location of these components during an actual recharge session. In general, system 200 of FIG. 5 may operate in a manner substantially similar to system 100 of FIG. 1.

For example, IMD 110 may be implanted within pocket 104 and include a rechargeable battery 112. Inductive charging unit 130 may transmit an alternating current signal across cable 134 to primary coil 132. Primary coil 132 may generate a magnetic field which may induce a current in secondary coil 113, recharging battery 112. A heat exchanger 30, including heat exchanging unit 120, tubing 124A-124B, and heat sink chamber 122 may be interposed between primary coil 132 and region of skin 106 to actively cool the region of skin 106 below the normal ambient temperature of the skin. In some examples, the operation of IMD 110, inductive charging unit 130, and heat exchanging unit 120 may be controlled by external programmer 140.

In some examples, system 200 may cool the region of skin 106 to a constant temperature to maintain the temperature of pocket 104 to below a temperature that may damage tissue. In other words, even with a temperature gradient cooler at the surface of skin 106 and warmer adjacent IMD 110, the tissue adjacent IMD 210 may still be below a temperature at which damage could occur during the recharge session. For example, it has been observed that cooling the region of skin 106 proximate to IMD 110 to a temperature between approximately 15 to 18 degrees Celsius will prevent the temperature of pocket 104 from rising to a harmful temperature (e.g., higher than 39 degrees Celsius or 43 degrees Celsius), even at extremely high rates of recharge (e.g., 2800 mW). In other examples, the potentially damaging temperature may be calculated based on the amount of time necessary for recharging since tissue may be capable of withstanding warmer temperatures for shorter periods of time. In other examples, it may be observed that maintaining the region of skin 106 within a temperature range of 15 to 25 degrees Celsius is sufficient to prevent IMD 110 or pocket 104 from exceeding a safe temperature and prevent inducing undesirable heating of the tissue of the patient.

As shown in FIG. 5, system 200 may use a feedback mechanism to control the temperature of skin 106 by sampling the temperature of one or more locations and adjusting the active cooling from heat exchanging unit 120 based upon the sampled temperatures. In this way, system 200 may dynamically adjust the skin temperature, or even the rate of cooling, to maintain the temperature of various locations from reaching unsafe temperatures.

For example, system 200 may include one or more temperature sensors 250A-250F (collectively, temperature sensors 250) for monitoring temperature. In one example, IMD 110 may include a temperature sensor 250A on the housing of IMD 110 most distal to heat sink chamber 122 of the heat exchanger 30 (e.g., the portion of the IMD 110 farthest from the cooling effects of the heat exchanger 30). In one example, the temperature sensor 250A is affixed to the exterior of the housing of IMD 110. In another example, the temperature sensor 250A is integrated into the housing of IMD 110. In yet another example, the temperature sensor 250A is affixed to the interior of the housing of IMD 110. Thus, temperature sensor 250A may monitor the temperature of the portion of IMD 110 most distant, or facing away, from heat sink chamber 222. This location of tissue on the far side of IMD 110 with respect to heat sink chamber 122 may have the highest temperature during recharge because it is furthest from heat sink chamber 122. In some examples, temperature sensor 250A may be positioned on the superficial surface of the IMD housing. In other examples, an additional temperature sensor may be provided for monitoring a portion of the IMD that is closest to the cooling effects of the heat exchanger 30 using any of the aforementioned techniques. In another example, system 200 may include a temperature sensor 250B positioned within pocket 104 and connected to IMD 110 via a cable or other electrical tether. In other examples, sensor 250B may be wirelessly coupled to IMD 110, heat exchanging unit 120, inductive charging unit 130, and/or external programmer 140. Thus, temperature sensor 250B may monitor the internal temperature of pocket 104. In another example, IMD 110 may include an internal temperature sensor 250C within the housing of IMD 110. Temperature sensor 250C may thus monitor the temperature within the IMD, such as the temperature of secondary coil 113, battery 112, or the inside surface of the IMD housing. In a further example, system 200 may include a temperature sensor 250D positioned on the exterior surface of skin 106 above IMD 110. Temperature sensor 250D may be connected to primary coil 132 via a cable or may instead be a stand-alone device (e.g. a sensor that is carried by a patch affixed to the skin) that wirelessly communicates with inductive charging unit 130 and/or IMD 110. Thus, temperature sensor 250D may monitor the temperature of the skin 106 of the patient near IMD 110 and primary coil 132. In a further example, heat sink chamber 122 may include a temperature sensor 250E affixed to the exterior of the surface of a housing of heat sink chamber 122, integrated into the housing of the heat sink chamber 122, or affixed to an interior of the housing of heat sink chamber 122 for monitoring the temperature of heat sink chamber 122, the skin 106 of the patient, and/or primary coil 132. In a further example, primary coil 132 may include a temperature sensor 250F for monitoring the temperature of primary coil 132. These and/or other temperature sensors may be included within system 200 for determining the temperature of respective locations within system 200 and the patient. However, the techniques of the disclosure are not limited to these locations. Rather, temperature sensors may be positioned in numerous other locations of system 200 not depicted herein, such as within inductive charging unit 130, heat exchanging unit 120, or the tissue of patient 102, to implement the techniques of the disclosure. In some examples, temperature sensors 250 may be thermocouples, resistive temperature devices (e.g., RTDs or thermistors), infrared radiators, bimetallic devices, liquid expansion devices, molecular change-of-state sensors, and silicon diodes. The techniques of the disclosure may be implemented with any type of sensor capable of measuring the temperature of the various components of system 200.

According to the techniques of the disclosure, system 200 may monitor the temperatures recorded by temperature sensors 250. If the temperature of one or more temperatures sensors 250 exceeds a predetermined temperature, system 200 may increase the rate at which heat exchanging unit 120 cools the region of skin 106 of patient 102 and/or decrease the power with which inductive charging unit 130 charges the battery 112 of IMD 110 (e.g., if the cooling rate cannot be further increased). In one example, system 200 may have a single temperature sensor 250A, which monitors the temperature of the portion of IMD 110 most distant from the cooling effects of heat sink chamber 122. If system 200 determines that the temperature measured by temperature sensor 250A exceeds the predetermined threshold, damage to patient tissue could occur at that location or another location of the patient. Accordingly, system 200 may operate to increase the rate of cooling performed by heat exchanging unit 120 such that the temperature measured by temperature sensor 250A falls back below the predetermined threshold temperature. In one example, the predetermined threshold temperature is 39 degrees Celsius. In another example, the predetermined threshold temperature is 37 degrees Celsius. In still other scenarios, the predetermined threshold temperature is selected from a range of 34-39 degrees Celsius.

In another example, system 200 may have more than one temperature sensor, such as temperature sensors 250A, 250B, and 250C. In this example, if system 200 determines that the temperature measured by any one of temperature sensors 250A, 250B, and 250C exceeds 39 degrees Celsius, it may operate to increase the rate of cooling performed by heat exchanging unit 120 such that no temperature measured by any one of temperature sensors 250A, 250B, and 250C exceeds 39 degrees Celsius. Alternatively, system 200 may model temperature gradients throughout the tissue based on the measured temperatures to determine if any tissue could be exceeding the predetermined temperature threshold.

In another example, system 200 may have more than one temperature sensor, such as temperature sensors 250A, 250B, and 250E. In this example, system 200 may assign a different predetermined temperature to each temperature sensor. For example, temperature sensors 250A and 250B, which are positioned within surgical pocket 104, may have a predetermined temperature of 39 degrees Celsius, while temperature sensor 250E, positioned against the skin of patient 102, may have a much lower predetermined temperature (e.g., 32 degrees Celsius). In this example, if system 200 determines that the temperature measured by any one of temperature sensors 250A, 250B, and 250C exceeds the corresponding predetermined temperature, it may operate to increase the rate of cooling performed by heat exchanging unit 120 such that no portion of the tissue of patient 102 exceeds 39 degrees Celsius. For example, system 200 may model temperature gradients based on the measured temperature at the surface of the skin of patient 102 to determine if any tissue within pocket 104 could be exceeding 39 degrees Celsius.

In a further example, system 200 may have a single temperature sensor 250D for monitoring the temperature of the region of skin 106 proximate to IMD 110. As discussed above, it has been observed that cooling the region of skin 106 proximate to IMD 110 to a temperature between 15 to 18 degrees Celsius will prevent the temperature of tissue adjacent IMD 110, including tissue associated with pocket 104, from rising to a harmful temperature (e.g., higher than 39 degrees Celsius) even at extremely high rates of energy transfer during recharge (e.g., 2800 mW). Thus, in this example, if system 100 determines that the temperature measured by temperature sensor 250D exceeds 18 degrees Celsius, it may responsively operate to increase the rate of cooling performed by heat exchanging unit 120 such that the temperature of the region of skin 106 is reduced below 18 degrees Celsius. In a further example, system 200 may include temperature sensor 250C and temperature sensor 250D and operate to increase the rate of cooling performed by heat exchanging unit 120 such that the temperature measured by temperature sensor 250C does not exceed 39 degrees Celsius while the temperature measured by temperature sensor 250D does not exceed 18 degrees Celsius. In still further examples, the temperature of IMD 110 may be measured, and the cooling of the region of skin 106 may be increased or decreased to prevent the temperature of IMD 110 from exceeding a predetermined value selected from a temperature range of 34 to 39 degrees Celsius.

The architecture of system 200 illustrated in FIG. 5 is shown for exemplary purposes only. The techniques as set forth in this disclosure may be implemented in the example system of FIG. 5, as well as other types of systems not described specifically herein. In other examples, system 200 may have a single temperature sensor, or any combination of one or more temperature sensors 250A-250F. Further, in other examples, heat exchanger 30, via one or more internal processors, memory, and temperature sensor 250E, may regulate its own operation, as opposed to receiving commands or instructions from one or more of IMD 110, external programmer 140, and charging unit 20. Nothing in this disclosure should be construed so as to limit the techniques of this disclosure to the example system illustrated by FIG. 5.

Accordingly, it may be seen that a system according to the techniques of the disclosure may allow for active cooling of the skin of a patient. Thus, the system may cool the primary coil of an inductive charger and the surgical pocket within which an IMD is implanted, such that the system prevents the temperature of the tissue of the patient from reaching undesirable temperatures. Thus, a system according to the techniques of the disclosure may allow for the inductive charging of an IMD at a rate much higher than other systems because the heat generated by fast rates of recharge is removed from the system before it can accumulate causing damage to the tissue of the patient. Further, the system of the present disclosure may allow for dynamic cooling of the skin of the patient to respond to changes in temperature measured by at least one temperature sensor. Accordingly, the system of the present disclosure may allow for much higher rates of charging than other systems.

Figure 6B:
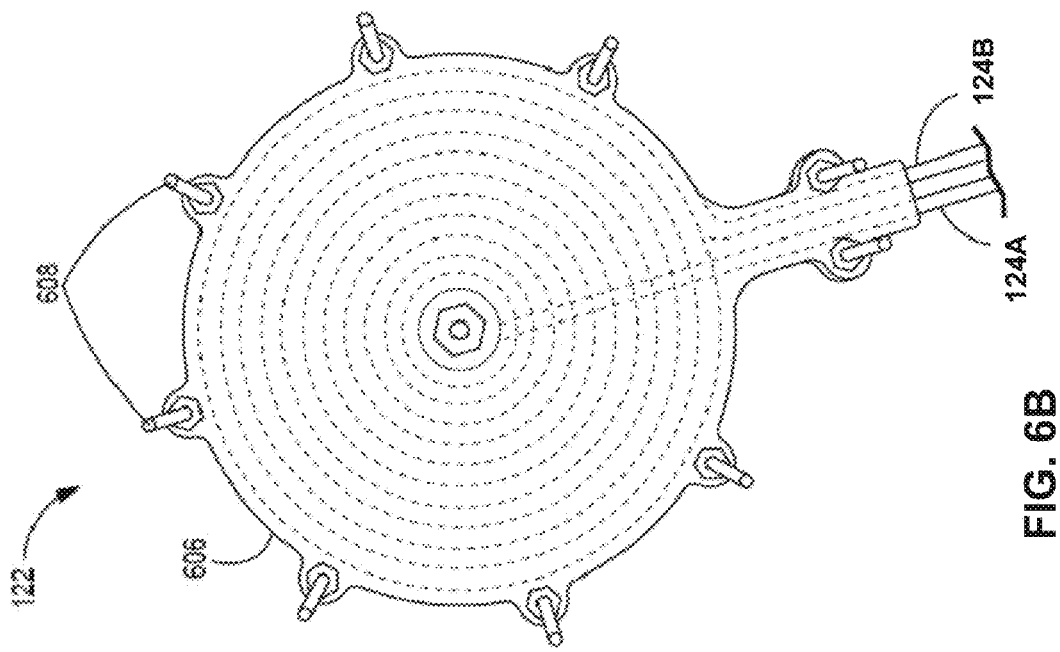
FIG. 6B is an illustration of an example heat sink chamber according to the techniques of the disclosure.
Figure 6A:
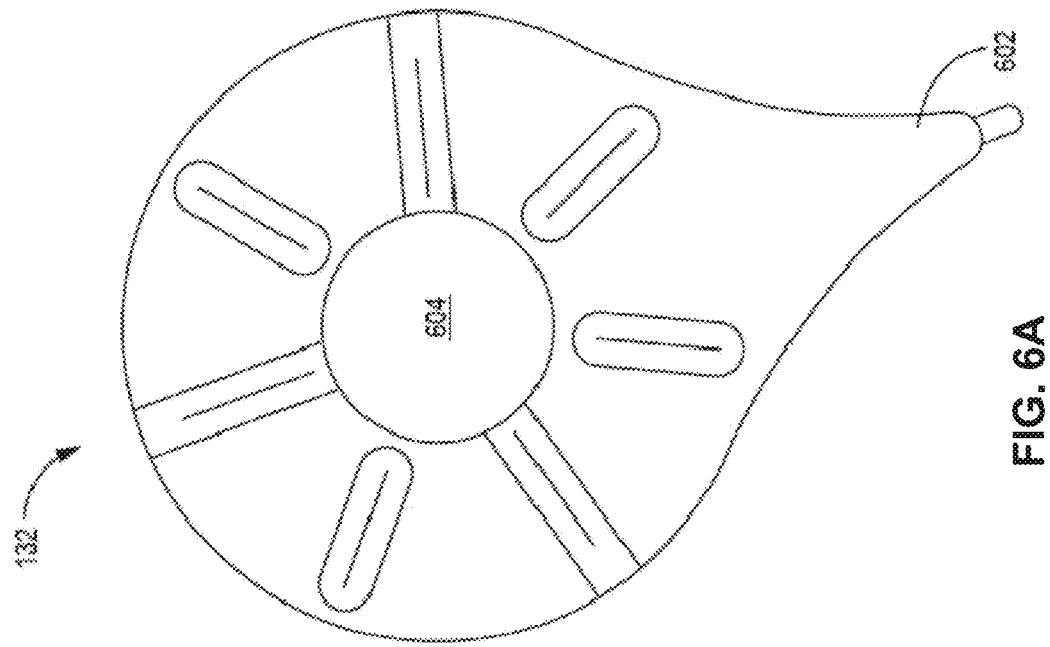
FIG. 6A is an illustration of an example primary coil of an inductive recharger.

FIG. 6A is an illustration of an example primary coil (e.g., primary coil 132 of FIG. 1) of an inductive recharger. In some examples, the primary coil 132 may include multiple turns of a conductive material, such as copper wiring, wound around a core 604. In some examples, the core may be a solid insulating material, while in other examples, the multiple turns of the conductive material are wound so as to define a central opening or hollow core 604. In some examples, the turns of conductive material may be encapsulated in a magnetically permeable polymer sheath. In some examples, the primary coil 132 may include an anode and cathode for transmitting an alternating current along the conductive material. The primary coil 132 may receive electrical current from an inductive charging unit 130 (not shown). In some examples, primary coil 132 includes a mounting point 602 configured to adapt to cable 134 and receive the alternating current signal from inductive charging unit 130 via cable 134.

FIG. 6B is an illustration of an example heat sink chamber 122 according to the techniques of the disclosure. In some examples, the heat sink chamber 122 may include a first length of tubing 124A for allowing fresh coolant to flow in, and a second length of tubing 124B for allowing heated coolant to flow out. In one example, the tubing 124 is wound in a shape such that fluid flows parallel to the region of skin of a patient to be cooled. In some examples, this shape may be a maze, spiral, or other pattern selected for its effectiveness in removing heat from the surface area of the skin. In some examples, the tubing 124 receives structural strength by being encased within a case or housing 606 (e.g., a case constructed of polymer or metal). In one example, the polymer case is magnetically permeable, so as not to interfere with the magnetic field created by the primary coil 132 of the inductive charger. The example of FIG. 6B, the polymer case may be configured so as to connect to the primary coil 132 illustrated in FIG. 6A. For example, heat sink chamber 122 may include mounting pins 608 for affixing heat sink chamber 122 to primary coil 132. Alternatively, head sink chamber 122 and primary coil 132 may be affixed or otherwise attached to each other via hook and loop closures, interlocking indents and detects, a threaded connection, a sleeve that couples the two elements together, or any other affixing mechanism. Heat sink chamber 122 and primary coil 132 may be removably affixed in order to allow the two elements to be attached and separated as needed. In other examples, the case or housing of the heat sink chamber may be formed to include a fluid path instead of enclosing separate tubing.

The architecture of the primary coil 132 in FIG. 6A and the heat sink chamber 122 in FIG. 6B are shown for exemplary purposes only. The techniques as set forth in this disclosure may be implemented in the example system of FIGS. 6A and 6B, as well as other types of systems not described specifically herein. For example, the primary coil 132 and heat sink chamber 122 may be of different shapes or sizes (i.e., circular, oval, rectangular, octagonal). Further, the heat sink chamber 122 may be configured so as to be adaptable to the primary coil 132, or they may not be configured to connect to one another. Further, the heat sink chamber 122 and primary coil 132 may be separate elements or integrated within the same component. These configurations of the primary coil 132 and heat sink chamber 122 in FIGS. 6A and 6B are examples, but other configurations having different sizes, shapes, and materials may be used in other examples. The heat sink chamber 122 may provide an area similar that of the primary coil 132. In some examples, the heat sink chamber 122 may have a larger area than the primary coil 132 or a smaller area than the primary coil 132. The heat sink chamber 122 may also include one or more mating surfaces that help lock or fit the heat sink chamber 122 to the primary coil 132.

Figure 7:
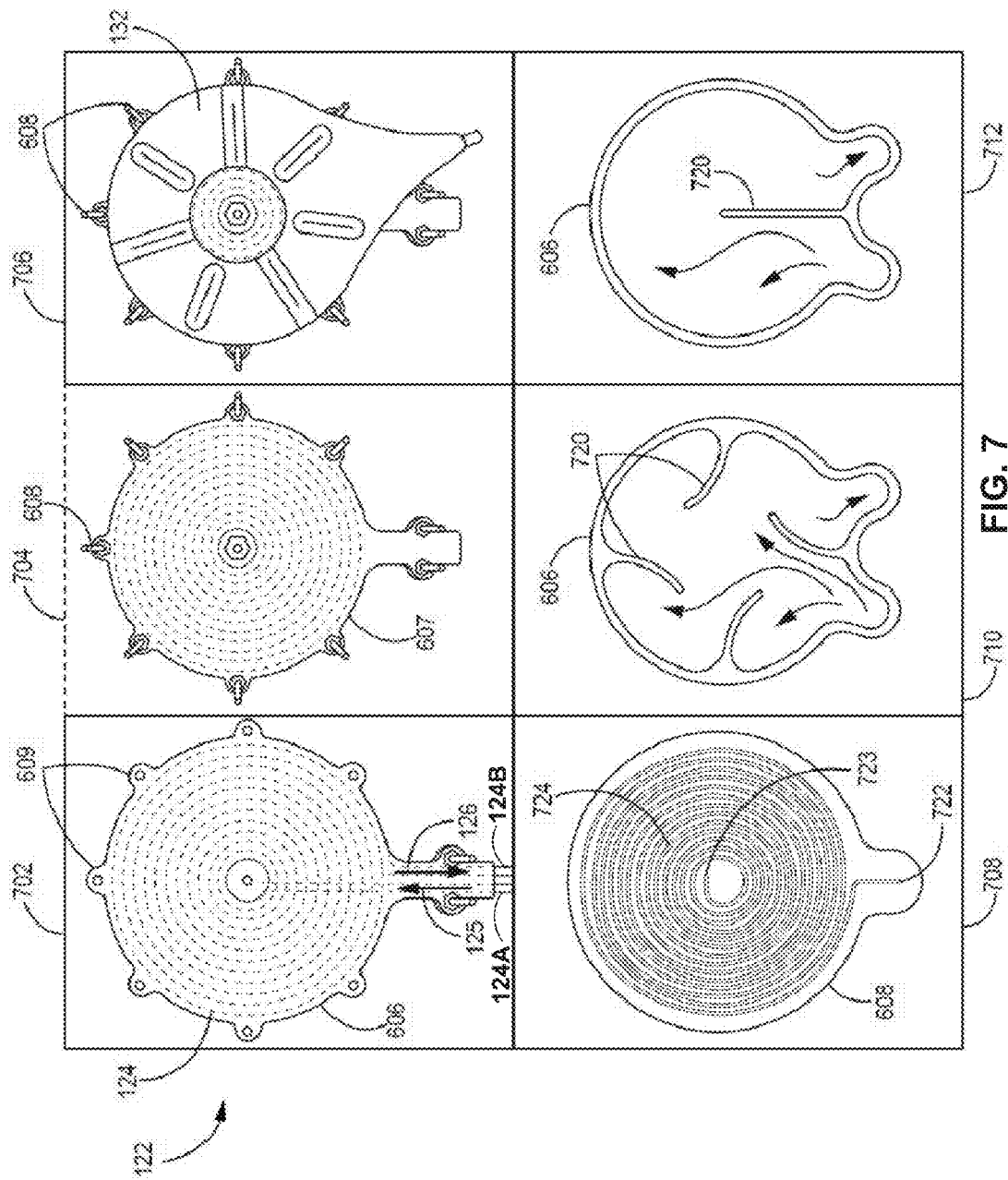
FIG. 7 is an illustration of example heat sink chambers according to the techniques of the disclosure

FIG. 7 is an illustration of example heat sink chambers according to the techniques of the disclosure. In one example, heat sink chamber 122 of diagram 702 includes a length of tube 124 wound in a spiral and given structural support by a polymer shell 606. In this example, fresh coolant may flow into one end of the tube along path 125, collect heat as it flows through the spiral shape of the heat sink chamber, and the heated coolant may flow out of the other end of the tube via path 126. In this example, both the tube 124 and polymer shell 606 may be selected from a group of materials chosen for their magnetic permeability and thermal conductivity. In this example, polymer shell 606 is a female portion configured to mate with a polymer male portion 607 of diagram 704 via mounting pins 608 and mounting receptacles 609. Thus, male portion 606 and female portion 607 are configured to encapsulate tube 124 to provide structural support for tube 124.

In another example, heat sink chamber 122 of diagram 706 is configured to adapt to a primary coil 132 of an inductive charger. Thus, heat sink chamber 122 and primary coil 132 may connect together (e.g., in a stacked configuration) to form a single unit. In some examples, the female polymer shell portion 606 and the male polymer shell portion 607 are configured to encapsulate both tubing 124 and primary coil 132. In another example, female polymer shell portion 606 and the male polymer shell portion 607 are configured to encapsulate tubing 124, and the heat sink chamber 122 is configured to attach to the surface of primary coil 132.

In further examples, heat sink chamber 122 may eliminate the tubing and provide the channels of flow for the coolant. For example, in diagram 708, heat sink chamber 122 may be formed or constructed to provide an inlet 722 and outlet 723 and provide a spiral pattern of flow 724 for coolant received by the heat sink chamber. The spiral channel of heat sink chamber 122 may be formed of a constant diameter or cross-sectional area throughout the spiral channel or, in other examples, the diameter or cross-sectional area may increase or decrease in the direction of the flow through the spiral channel. Inlet 722 and outlet 723 may be configured to adapt to tubing 124 such that heat exchanging unit 120 provides fresh coolant into inlet 722 and receives heated coolant via outlet 723.

The example diagrams 710 and 712 provide further examples of structural configurations of heat sink chamber 122 wherein the flow of the coolant is disturbed such that the entire region of the heat sink chamber 122 receives some amount of coolant flow. In this way, one or more structures or baffles 720 of the design of the heat sink chamber 122 may cause turbulent flow or otherwise create flow that limits stagnant regions that receive little fresh coolant flow. In other words, the structures 720 may promote fluid flow throughout the entire volume of the heat sink chamber 122 that improve the removal of heat from the patient instead of allowing hot spots to accumulate that prevent adequate cooling of the entire surface area of the heat sink chamber 122.

For purposes of illustration, in FIG. 7, tube 124A is described as having an inlet 722 for providing fresh coolant flow to the heat sink chamber 122 along path 125. Similarly, tube 124B is described as having an outlet 723 for removing heated coolant flow from the heat sink chamber 122 along path 126. It will be understood that, in some examples, the direction of fluid flow through each of the example heat sink chambers 122 may be the reverse of the examples provided. A clinician may select the direction of fluid flow through each of the example heat sink chambers 122 to provide the greatest dispersion of heat through the example heat sink chambers 122.

The architecture of FIG. 7 is shown for exemplary purposes only. The techniques as set forth in this disclosure may be implemented in the example system of FIG. 4, as well as other types of systems not described specifically herein. For example, the primary coil 132 and heat sink chamber 122 may be of different shapes or sizes (i.e., circular, oval, rectangular, octagonal). Further, the heat sink chamber 122 may be configured so as to be adaptable to the primary coil 132, or they may not be configured to connect to one another. Further, the heat sink chamber 122 and primary coil 132 may be separate elements or integrated within the same component. In some embodiments, the primary coil 132 may be integrated into a housing that contains some or all of the other components of charging device 20 rather than being housed in a separate antenna structure. In this embodiment, the heat sink chamber 122 may likewise be integrated into this same housing, which may be handheld. Additionally, heat sink chamber 122 may detachably couple to the housing using any of the mechanisms discussed herein, or heat sink chamber 122 may be configured to remain detached from heat sink chamber 122. Further, the heat sink chamber 122 may incorporate a variety of flow patterns, such as spiral or maze, as well as various ridges, baffles, and grooves, to ensure that adequate coolant flow reaches the entire surface area of the heat sink chamber 122. Nothing in this disclosure should be construed so as to limit the techniques of this disclosure to the example devices illustrated by FIG. 7.

Figure 8:
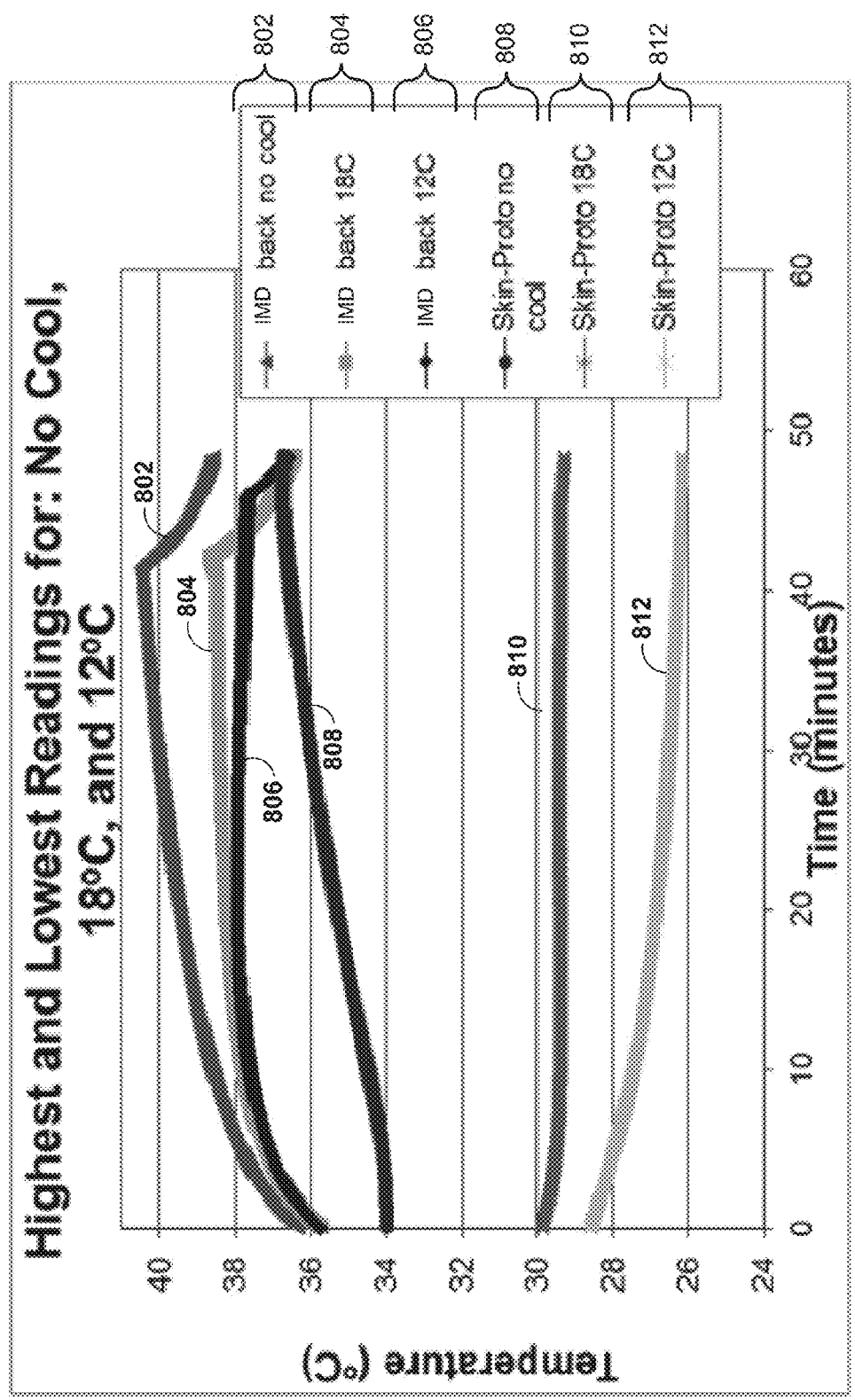
FIG. 8 is a graph comparing the heat generated by an example recharging system according to the techniques of the disclosure to other recharging systems.

FIG. 8 is a graph comparing the heat generated by an example recharging system (e.g., system 100 of FIG. 1) according to the techniques of the disclosure with various levels of cooling. In the example of FIG. 5, three different IMD recharging techniques operate at the maximum allowable recharge rate permitted by the technique. During operation, the temperature of an IMD 110 and the surface of a skin prototype are measured for each technique. In the first trial, the IMD recharging system does not use actively cooling techniques to cool the skin of the patient. Line 802 represents the temperature at the IMD 110, while line 808 represents the temperature at the interface of the skin and the heat-exchanger 30. It may be seen that in this example, the temperature of the IMD 110 shown in line 802 peaks above 41 degrees Celsius after 45 minutes of recharging while the temperature of the surface of the skin prototype in line 808 rises to almost 37 degrees Celsius after 45 minutes of charging. Thus, if no active cooling was used during recharge of the IMD 110 of a patient, tissue damage could occur due to the temperature of the tissue near the IMD 110 rising above the predetermined threshold of 39 degrees Celsius.

In the second example of FIG. 8, the techniques of the disclosure are used to actively cool the skin of the patient and prevent the temperature of the IMD 110 from exceeding 39 degrees Celsius. In this example using active cooling such that the temperature of the heat sink chamber is approximately 18 degrees Celsius, the temperature of the surface of the skin in line 810 is cooled from approximately 30 degrees Celsius to approximately 29 degrees Celsius during the recharge session. Accordingly, the temperature of the IMD 110 in line 804, and adjacent tissue, is prevented from exceeding 39 degrees Celsius. While normal body temperature is approximately 37 degrees, the body may safely tolerate a temperature of 39 degrees Celsius almost indefinitely. In this example, IMD temperatures remaining below 39 degrees Celsius would indicate that tissue damage would be avoided due to the cooling mechanism even though the inductive recharger is operating at maximum power for an indefinite amount of time. It is noted that tissue may tolerate temperatures higher than 39 degrees Celsius, but these higher temperatures may only be tolerable for a certain period of time before tissue begins to be damaged.

In the third example of FIG. 8, the techniques of the disclosure are used to actively cool the skin of the patient which prevents the temperature of the IMD from exceeding 38 degrees Celsius. In this example using active cooling such that the temperature of the heat sink chamber is approximately 12 degrees Celsius, the temperature of the surface of the skin prototype in line 812 is cooled from approximately 29 degrees Celsius to approximately 26 degrees Celsius. Thus, the temperature of the IMD in line 806 is prevented from exceeding 38 degrees Celsius during the recharge session. While normal body temperature is approximately 37 degrees, the body can safely tolerate 38 degrees Celsius almost indefinitely. In this example, if the system were operated inside a patient, undesirable heating of the tissue is avoided due to the cooling mechanism, even though the inductive recharger is operating at maximum power.

In some examples, the system may begin actively cooling the skin at the same time that the inductive charging unit begins to transfer energy to the battery of the IMD. In other examples, the system may first cool the skin (e.g., for a certain period of time or to the desired temperature) and then begin transferring energy by generating current in the primary coil. In this manner, the system may start the charging session with the tissue already cool instead of retroactively reducing the already heated tissue. In still further examples, the system may adjust active cooling of the skin in response to commands from the patient 102. Such commands may include increasing, decreasing, starting, or stopping the active cooling to accommodate the temperature preferences of the patient. For example, the user may turn the system on or off as desired to maintain appropriate temperatures during the recharging process.

Figure 9:
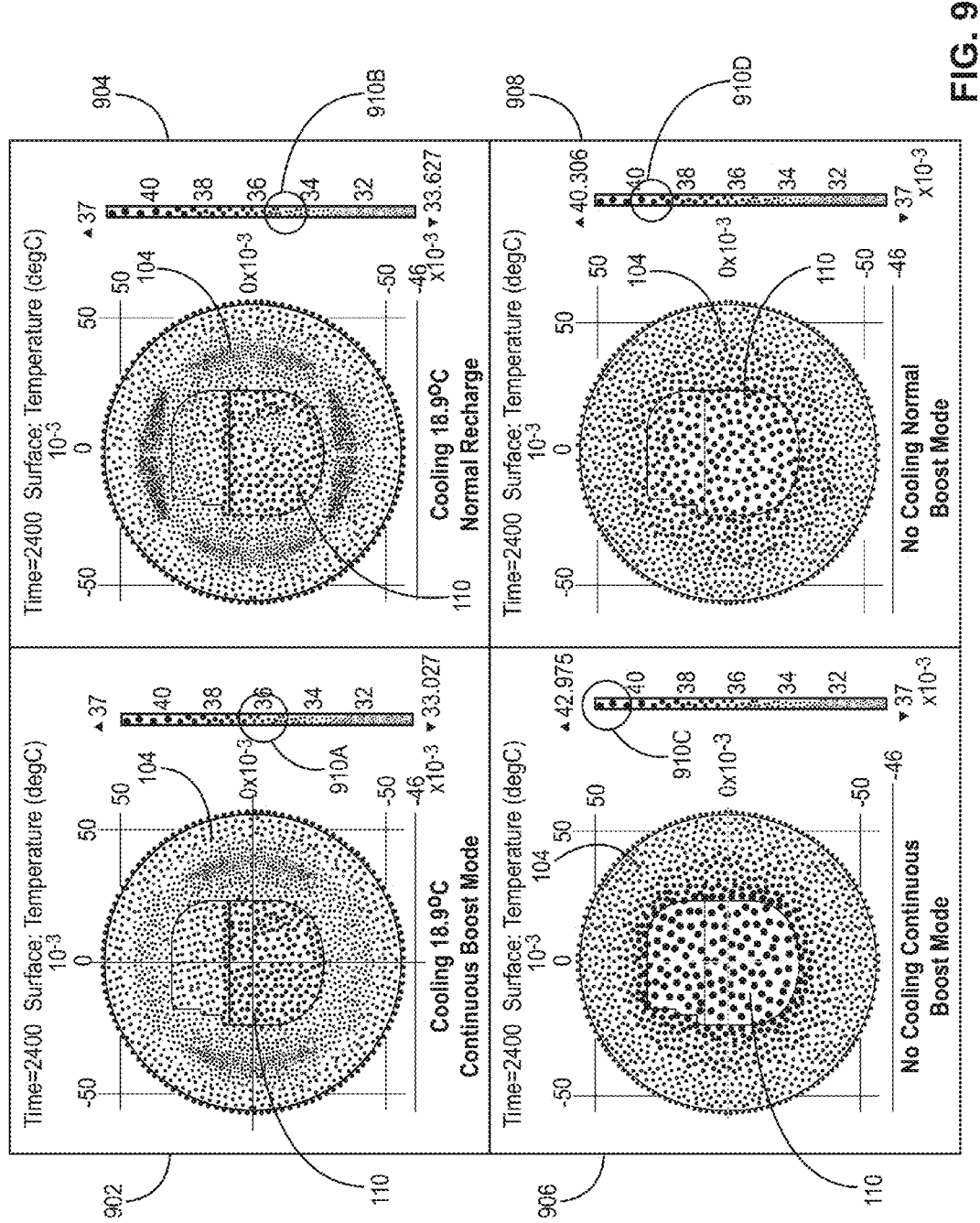
FIG. 9 is an illustration of the heat generated by an example recharging system according to the techniques of the disclosure compared to other recharging systems.

FIG. 9 is an illustration of the heat generated by an example recharging system operating with and without active cooling during a recharge system. Diagrams 906 and 908 illustrate the temperatures of an IMD 110 and surrounding tissue 104 without active cooling under boost mode and normal recharge mode, respectively. Boost mode may be recharging IMD 110 at a high or maximum energy transfer rate, whereas the normal recharge mode may be a lower energy transfer rate at which temperatures can be maintained indefinitely. In the normal recharge mode of diagram 908, the temperature of IMD 110 reaches a maximum 910D of 40.3 degrees Celsius and the surrounding tissue reaches a maximum of 39 degrees Celsius. Thus, without the techniques of the present disclosure, the IMD 110 of diagram 908 potentially could induce undesirable heating of the tissue of the patient, even operating at normal recharge rates. In the example of a system not using the techniques of the disclosure and operating at its maximum recharge for an indefinite amount of time ("continuous boost mode") (906), it may be seen that the temperature of an IMD reaches a maximum 910C of 43.0 degrees Celsius and the surrounding tissue reaches a maximum of 41 degrees Celsius. Thus, without the techniques of the present disclosure, the IMD 110 of system 906 may induce undesirable heating of the tissue of the patient.

In contrast, diagrams 902 and 904 illustrate the temperatures of an IMD 110 and surrounding tissue 104 using the techniques of the present disclosure to perform active cooling under boost mode and normal recharge mode, respectively. In the normal recharge mode of diagram 904, the temperature of IMD 110 reaches a maximum 910B of 35 degrees Celsius and the surrounding tissue reaches a maximum of 35 degrees Celsius. Similarly, In the example of a system not using the techniques of the disclosure and operating at its maximum recharge ("continuous boost mode") (906), it may be seen that the temperature of an IMD reaches a maximum 910A of 37 degrees Celsius and the surrounding tissue reaches a maximum of 35 degrees Celsius. Because the body may withstand temperatures of 37 degrees Celsius for indefinite periods of time, the systems of diagrams 902 and 904 may operate for indefinite periods of time without inducing undesirable heating of the tissue of the patient.

Accordingly, it may be seen that actively cooling of the skin of a patient reduces the temperature of both the IMD 110 and the surrounding tissue. Thus, the system may cool the primary coil of an inductive charger and the surgical pocket within which an IMD is implanted, such that the system prevents the temperature of the tissue of the patient from reaching undesirable temperatures. Thus, a system according to the techniques of the disclosure may allow for energy transfer by inductive charging much higher than other systems, or may allow for high charging for indefinite periods of time.

Figure 10:
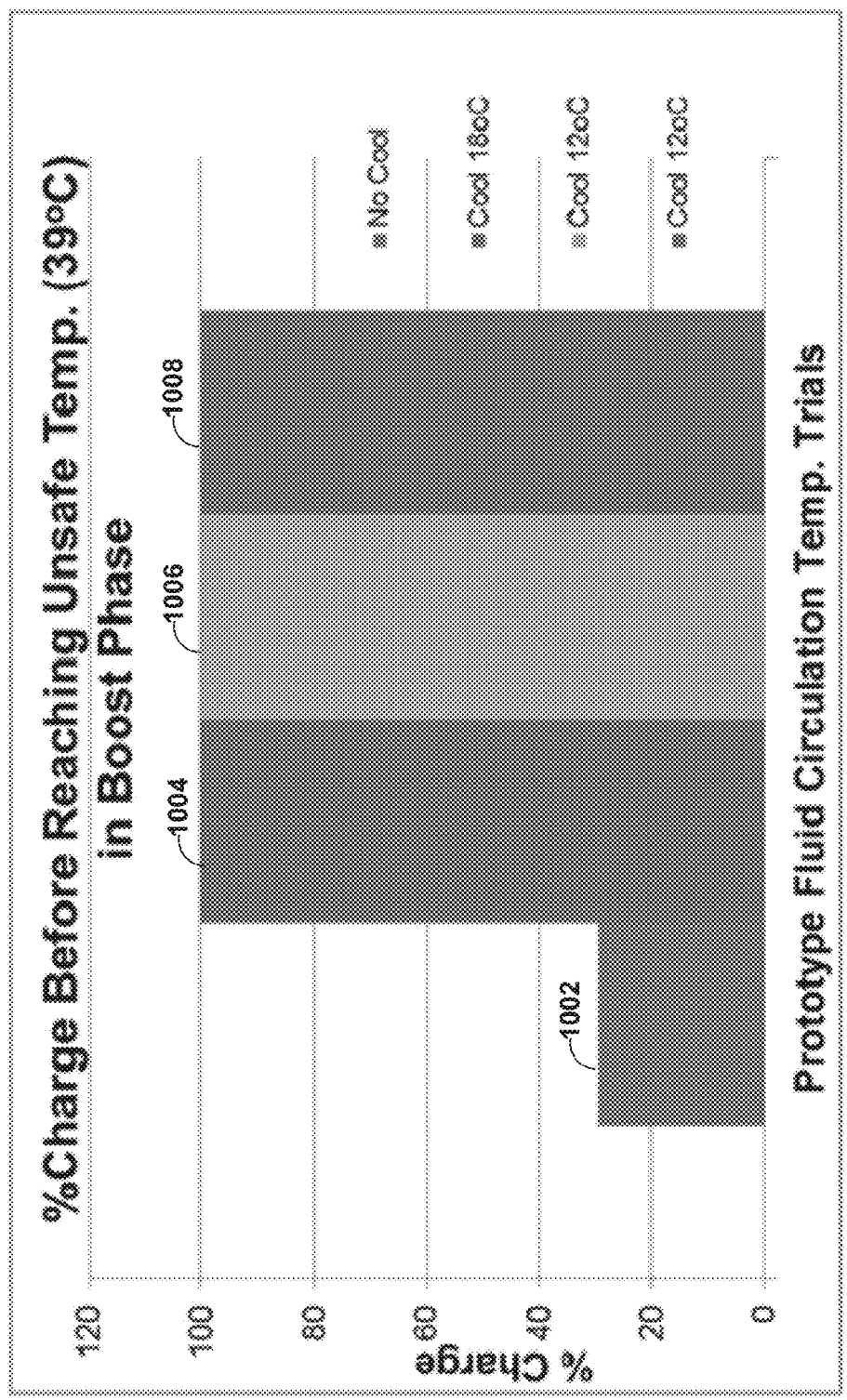
FIG. 10 is a graph comparing the charge completed before reaching an unsafe temperature for example recharging systems according to the techniques of the disclosure and other recharging systems.

FIG. 10 is a graph comparing the battery charge completed in an example IMD before reaching an unsafe temperature for example recharging systems with and without active cooling. As shown in FIG. 10, an example system (e.g., system 100 of FIG. 1) is operated in boost mode (e.g., the maximum rate of energy transfer and battery recharge possible by the inductive charging unit). In the example of FIG. 10, the system is capable of operating at a maximum recharge rate of 2800 mW. However, the techniques of the disclosure may also be suitable for recharge rates higher than 2800 mW. The temperature of the IMD 110 is monitored, and when it exceeds an undesirable temperature (e.g., 39 degrees Celsius), the system terminates the battery recharge session. The level of charge of the battery of the IMD was then measured to determine how much charge was delivered to the battery under each condition before the undesirable temperature was reached.

Without any active cooling, as shown by bar 1002, the recharge system caused the IMD 110 to quickly exceed the desired temperature threshold and was shut off. In this example of no active cooling, the system was able to deliver only about 30% of the energy required to fully charge the battery of the IMD before the temperature threshold was reached. Thus, without active cooling, the system may need to reduce the energy transfer rate, or terminate recharge completely, before the IMD battery is fully charged until the temperature of the tissue reduces back to normal body temperature.

By actively cooling the skin to either 12 degrees Celsius or 18 degrees Celsius, the system is able to fully charge the IMD battery before the tissue temperature reaches undesirable levels. In the example of bar 1004, a system using the techniques of the present disclosure can actively cool the surface of the skin of a patient to 18 degrees Celsius. This temperature keeps the IMD temperature below an undesirable temperature throughout the boost charging cycle, thus achieving delivery of 100% charge to the battery of the IMD in the boost recharge session. Similarly, in the third and fourth examples of bars 1006 and 1008, respectively, the system using active cooling of the surface of the skin of a patient to 12 degrees Celsius kept the IMD below an undesirable temperature throughout the boost charging cycle. Therefore, the systems using active cooling were able to deliver 100% charge to the battery of the IMD when providing continuous boost charging.

Figure 11:
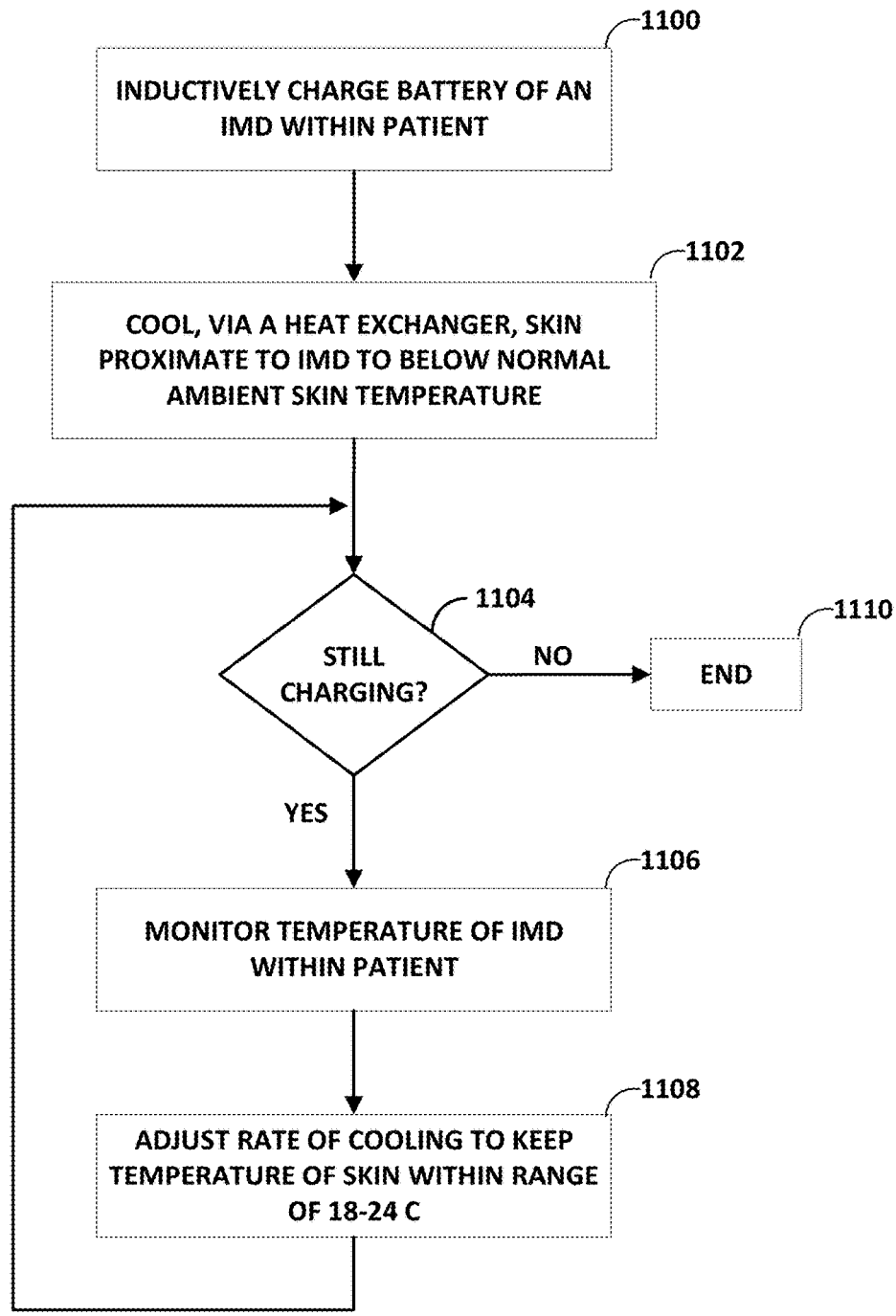
FIG. 11 is a flowchart illustrating an example operation for recharging an IMD according to the techniques of the disclosure.

FIG. 11 is a flowchart illustrating an example operation for recharging an IMD 110 according to the techniques of the disclosure. For convenience, the operation of FIG. 11 is described with respect to the components and circuitry of system 200 of FIG. 5. In the example of FIG. 11, a charging device 20 inductively charges a battery 112 of IMD 110 implanted within a surgical pocket 104 of patient 102 (1100).

Heat exchanger 30 cools skin 106 proximate to IMD 110 to a temperature below normal ambient skin temperature (1102). In some examples, heat exchanger 30 cycles a coolant from heat exchanging unit 120, through tubing 124 along path 125 into heat sink chamber 122, and back to heat exchanging unit 120 along path 126. The coolant within heat sink chamber 122 absorbs heat from primary coil 132 and skin 106, causing primary coil 132 and skin 106 to decrease in temperature while the coolant within heat sink chamber 122 increases in temperature. The heated coolant flows back through tubing 124 to heat exchanging unit 120, where it is re-cooled and recirculated to heat sink chamber 122.

External programmer 140 determines whether battery 112 of IMD 110 is still charging (1104). Upon determining that battery 112 of IMD 110 has not completed charging ("YES" branch of block 1104), external programmer 140 monitors the temperature of IMD 110 via one or more sensors 250 (1106). For example, programmer 140 may compare the measured temperature to one or more temperature thresholds. In response to determining that the measured temperature exceeds one or more of the temperature thresholds, external programmer 140 adjusts the rate of cooling by heat exchanger 30 to keep the temperature of skin 106 within a range of 18-24 degrees Celsius (1108). For example, upon determining that the temperature of skin 106 has fallen below 18 degrees Celsius, external programmer 140 instructs heat exchanger 30 to reduce the rate of cooling (e.g., by reducing the rate of flow of coolant through tubing 124. In another example, upon determining that the temperature of skin 106 has risen above 24 degrees Celsius, external programmer 140 instructs heat exchanger 30 to increase the rate of cooling (e.g., by increasing the rate of flow of coolant through tubing 124. In other examples, programmer 140 may employ other control algorithms, such as a proportional-integral-derivative (PID) controller or other technique to monitor the temperature and make appropriate corrections over time instead of just reacting to a threshold being exceeded. The cooling operation continues in a loop until external programmer 140 determines that charging is complete ("NO" branch of block 1104). Again, external programmer 140 determines whether battery 112 of IMD 110 has completed charging (1104). Upon determining that battery 112 of IMD 110 has completed charging, external programmer 140 terminates the charging process (1110).

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media. Non-transitory computer readable storage media is media which does not include propagating signals.

Various examples have been described. These and other examples are within the scope of the following claims.

What is claimed is:

1. A method comprising:
    charging, by an inductive charger, a rechargeable battery of an implantable medical device (IMD) within a patient, wherein the IMD comprises a housing that houses the rechargeable battery, and wherein a primary coil of the inductive charger is positioned above a region of skin of the patient proximate to the IMD; and
    cooling, by a heat exchanger, the region of skin to a temperature selected from a range of 5 degrees Celsius to 25 degrees Celsius, wherein an element of the heat exchanger is interposed between the primary coil and the region of skin.

2. The method of claim 1, further comprising measuring, by one or more processors, at least one first temperature of the IMD within the patient, and wherein cooling the region of skin to the temperature selected from the range of 5 degrees Celsius to 25 degrees Celsius comprises cooling the region of skin to the temperature selected from the range of 5 degrees Celsius to 25 degrees Celsius such that the at least one first temperature does not exceed a predetermined temperature.

3. The method of claim 2, wherein the predetermined temperature is selected from a range of 34 degrees Celsius to 39 degrees Celsius.

4. The method of claim 3, wherein the predetermined temperature further comprises a predetermined temperature selected to accommodate a temperature sensitivity of a specific patient.

5. The method of claim 2, wherein:
    the housing of the IMD comprises a first surface proximate to the element of the heat exchanger and a second surface distal to the element of the heat exchanger; and
    measuring the at least one first temperature of the IMD within the patient comprises measuring a temperature of the second surface of the IMD distal to the element of the heat exchanger.

6. The method of claim 2, wherein measuring the at least one first temperature of the IMD within the patient comprises measuring one temperature of a plurality of temperatures selected from a group comprising:
    an external surface temperature of the region of skin;
    a temperature of the housing of the IMD;
    a temperature of the battery of the IMD; and
    a temperature of an internal surgical pocket of tissue of the patient enveloping the IMD.

7. The method of claim 2, wherein measuring the at least one first temperature of the IMD within the patient comprises measuring each temperature of a plurality of temperatures of a group comprising:
    an external surface temperature of the region of skin;
    a temperature of the housing of the IMD;
    a temperature of the battery of the IMD; and
    a temperature of an internal surgical pocket of tissue of the patient enveloping the IMD.

8. The method of claim 7, wherein cooling the region of skin to the temperature selected from the range of 5 degrees Celsius to 25 degrees Celsius such that the at least one first temperature does not exceed the predetermined temperature comprises cooling the region of skin to the temperature selected from the range of 5 degrees Celsius to 25 degrees Celsius such that each measured temperature of the plurality of measured temperatures of the group does not exceed the predetermined temperature.

9. The method of claim 7, wherein cooling the region of skin to the temperature selected from the range of 5 degrees Celsius to 25 degrees Celsius such that the at least one first temperature does not exceed the predetermined temperature comprises cooling the region of skin to the temperature selected from the range of 5 degrees Celsius to 25 degrees Celsius such that at least one measured temperature of the plurality of measured temperatures of the group does not exceed the predetermined temperature.

10. The method of claim 1, wherein cooling the region of skin to the temperature selected from the range of 5 degrees Celsius to 25 degrees Celsius comprises cooling the region of skin to a temperature selected from a range of 15 degrees Celsius to 25 degrees Celsius.

11. The method of claim 10, wherein the temperature selected from a range of 15 degrees Celsius to 25 degrees Celsius comprises a temperature selected to accommodate a temperature sensitivity of a specific patient.

12. The method of claim 1, wherein cooling, by the heat exchanger, the region of skin comprises circulating, by the heat exchanger, a coolant through a heat sink chamber in contact with the region of skin.

13. The method of claim 12, wherein the heat sink chamber comprises a magnetically permeable polymer.

14. The method of claim 12, wherein the coolant is a fluid that comprises at least one of water or propylene glycol.

15. The method of claim 1, wherein the element of the heat exchanger is affixed to a housing of the primary coil.

16. A system comprising:
an implantable medical device (IMD) implantable within a surgical pocket of a patient, comprising:
a housing; and
a rechargeable battery within the housing;
an inductive charger configured to charge the rechargeable battery of the IMD, wherein the inductive charger comprises a primary coil configured to be positioned above a region of skin of the patient proximate to the IMD;
an element of a heat exchanger configured to be interposed between the primary coil and the region of skin; and
one or more processors configured to control the heat exchanger to cool the region of skin to a temperature selected from a range of 5 degrees Celsius to 25 degrees Celsius.

17. The system of claim 16, wherein the one or more processors are further configured to:
measure at least one first temperature of the IMD within the patient, and
control the heat exchanger to cool the region of skin to the temperature selected from the range of 5 degrees Celsius to 25 degrees Celsius such that the at least one first temperature does not exceed a predetermined temperature.

18. The system of claim 17, wherein the predetermined temperature is selected from a range of 34 degrees Celsius to 39 degrees Celsius.

19. The system of claim 18, wherein the predetermined temperature further comprises a predetermined temperature selected to accommodate a temperature sensitivity of a specific patient.

20. The system of claim 17, wherein:
the housing of the IMD comprises a first surface proximate to the element of the heat exchanger and a second surface distal to the heat exchanger; and
the one or more processors configured to measure the at least one first temperature of the IMD within the patient are further configured to measure a temperature of the second surface of the IMD distal to the element of the heat exchanger.

21. The system of claim 17, wherein the one or more processors configured to measure the at least one first temperature of the IMD within the patient are further configured to measure one temperature of a plurality of temperatures selected from a group comprising:
an external surface temperature of the region of skin;
a temperature of the housing of the IMD;
a temperature of the battery of the IMD; and
a temperature of an internal surgical pocket of tissue of the patient enveloping the IMD.

22. The system of claim 17, wherein the one or more processors configured to measure the at least one first temperature of the IMD within the patient are further configured to measure each temperature of a plurality of temperatures selected from a group comprising:
an external surface temperature of the region of skin;
a temperature of the housing of the IMD;
a temperature of the battery of the IMD; and
a temperature of an internal surgical pocket of tissue of the patient enveloping the IMD.

23. The system of claim 22, wherein the one or more processors configured to control the heat exchanger to cool the region of skin to the temperature selected from the range of 5 degrees Celsius to 25 degrees Celsius such that the at least one first temperature does not exceed the predetermined temperature are further configured to control the heat exchanger to cool the region of skin to the temperature selected from the range of 5 degrees Celsius to 25 degrees Celsius such that each measured temperature of the plurality of measured temperatures of the group does not exceed the predetermined temperature.

24. The system of claim 16, wherein the one or more processors configured to control the heat exchanger to cool the region of skin to the temperature selected from the range of 5 degrees Celsius to 25 degrees Celsius are further configured to control the heat exchanger to cool the region of skin to a temperature selected from a range of 15 degrees Celsius to 25 degrees Celsius.

25. The system of claim 24, wherein the temperature selected from a range of 15 degrees Celsius to 25 degrees Celsius comprises a temperature selected to accommodate a temperature sensitivity of a specific patient.

26. The system of claim 16, wherein the one or more processors configured to control the heat exchanger to cool the region of skin are further configured to control the heat exchanger to circulate a coolant through a heat sink chamber in contact with the region of skin.

27. The system of claim 26, wherein the heat sink chamber comprises a magnetically permeable polymer.

28. The system of claim 26, wherein the coolant is a fluid that comprises at least one of water or propylene glycol.

29. The system of claim 16, wherein the element of the heat exchanger is affixed to a housing of the primary coil.

30. A system comprising:
an implantable medical device (IMD) implantable within a surgical pocket of a patient, comprising:
a housing; and
a rechargeable battery within the housing;

means for charging the rechargeable battery of the IMD, wherein the means for charging the rechargeable battery of the IMD is configured to be positioned above a region of skin of the patient proximate to the IMD;

means for cooling skin between the means for charging and the IMD; and one or more processors configured to control the means for cooling the skin to cool the skin between the means for charging and the IMD to a temperature selected from a range of 5 degrees Celsius to 25 degrees Celsius.

31. The system of claim 30, wherein the one or more processors are further configured to:

measure at least one first temperature of the IMD within the patient, and control the means for cooling skin to cool the skin between the means for charging and the IMD to the temperature selected from the range of 5 degrees Celsius to 25 degrees Celsius such that the at least one first temperature does not exceed a predetermined temperature.

32. The system of claim 30, wherein the one or more processors configured to control the means for cooling the skin to cool the skin between the means for charging and the IMD to the temperature selected from the range of 5 degrees Celsius to 25 degrees Celsius are further configured to control the means for cooling the skin to cool the skin between the means for charging and the IMD to a temperature selected from a range of 15 degrees Celsius to 25 degrees Celsius.

* * * * *